US011033386B2

(12) United States Patent
Keidar

(10) Patent No.: US 11,033,386 B2
(45) Date of Patent: Jun. 15, 2021

(54) LOW PROFILE TRANSSEPTAL CATHETER AND IMPLANT SYSTEM FOR MINIMALLY INVASIVE VALVE PROCEDURE

(71) Applicant: Edwards Lifesciences Corporation, Irvine, CA (US)

(72) Inventor: Yaron Keidar, Haifa (IL)

(73) Assignee: Edwards Lifesciences Corporation, Irvine, CA (US)

( * ) Notice: Subject to any disclaimer, the term of this patent is extended or adjusted under 35 U.S.C. 154(b) by 185 days.

(21) Appl. No.: 16/351,402

(22) Filed: Mar. 12, 2019

(65) Prior Publication Data
US 2019/0209309 A1 Jul. 11, 2019

Related U.S. Application Data

(62) Division of application No. 15/018,781, filed on Feb. 8, 2016, now Pat. No. 10,231,834.
(Continued)

(51) Int. Cl.
*A61F 2/24* (2006.01)
*A61B 17/064* (2006.01)

(52) U.S. Cl.
CPC .......... *A61F 2/2427* (2013.01); *A61F 2/2409* (2013.01); *A61F 2/2412* (2013.01);
(Continued)

(58) Field of Classification Search
CPC .... A61B 17/064; A61F 2/2463; A61F 2/2409; A61F 2/2418
See application file for complete search history.

(56) References Cited

U.S. PATENT DOCUMENTS

| 3,755,823 A | 9/1973 | Hancock |
| 4,035,849 A | 7/1977 | Angell et al. |

(Continued)

FOREIGN PATENT DOCUMENTS

| CN | 102869321 A | 1/2013 |
| DE | 19532846 A1 | 3/1997 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal; No. 13. pp. 704-708. 1992.
(Continued)

*Primary Examiner* — Richard G Louis
(74) *Attorney, Agent, or Firm* — Edwards Lifesciences; Jeff B. Haendler

(57) ABSTRACT

A system for repairing a native heart valve can comprise a first fastener, a second faster, a first leaflet brace, and a second leaflet brace. The first leaflet brace can be configured to extend partially around a first native leaflet. The second leaflet brace can be configured to extend partially around a second native leaflet. The first fastener can be configured to be deployed on respective first end portions of the first and second braces so as to connect the first end portions to each other. The second fastener can be configured to be deployed on respective second end portions of the first and second braces so as to connect the second end portions to each other. When the first end portions are connected to each other and the second end portions are connected to each other, the first and second leaflet braces encircle the first and second native leaflets.

20 Claims, 49 Drawing Sheets

Related U.S. Application Data

(60) Provisional application No. 62/113,839, filed on Feb. 9, 2015.

(52) U.S. Cl.
CPC .......... *A61F 2/2418* (2013.01); *A61B 17/064* (2013.01); *A61F 2/2463* (2013.01)

(56) References Cited

U.S. PATENT DOCUMENTS

| | | | |
|---|---|---|---|
| 4,777,951 A | 10/1988 | Cribier et al. | |
| 4,787,899 A | 11/1988 | Lazarus | |
| 4,796,629 A | 1/1989 | Grayzel | |
| 4,856,516 A | 8/1989 | Hillstead | |
| 4,878,495 A | 11/1989 | Grayzel | |
| 4,966,604 A | 10/1990 | Reiss | |
| 4,994,077 A | 2/1991 | Dobben | |
| 5,059,177 A | 10/1991 | Towne et al. | |
| 5,192,297 A | 3/1993 | Hull | |
| 5,282,847 A | 2/1994 | Trescony et al. | |
| 5,370,685 A | 12/1994 | Stevens | |
| 5,411,552 A | 5/1995 | Andersen et al. | |
| 5,545,214 A | 8/1996 | Stevens | |
| 5,554,185 A | 9/1996 | Block et al. | |
| 5,558,644 A | 9/1996 | Boyd et al. | |
| 5,584,803 A | 12/1996 | Stevens et al. | |
| 5,591,195 A | 1/1997 | Taheri et al. | |
| 5,607,464 A | 3/1997 | Trescony et al. | |
| 5,665,115 A | 9/1997 | Cragg | |
| 5,769,812 A | 6/1998 | Stevens et al. | |
| 5,800,508 A | 9/1998 | Goicoechea et al. | |
| 5,840,081 A | 11/1998 | Andersen et al. | |
| 5,855,597 A | 1/1999 | Jayaraman | |
| 5,925,063 A | 7/1999 | Khosravi | |
| 6,027,525 A | 2/2000 | Suh et al. | |
| 6,168,614 B1 | 1/2001 | Andersen et al. | |
| 6,221,091 B1 | 4/2001 | Khosravi | |
| 6,245,102 B1 | 6/2001 | Jayaraman | |
| 6,302,906 B1 | 10/2001 | Goicoechea et al. | |
| 6,425,916 B1 | 7/2002 | Garrison et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,482,228 B1 | 11/2002 | Norred | |
| 6,582,462 B1 | 6/2003 | Andersen et al. | |
| 6,652,578 B2 | 11/2003 | Bailey et al. | |
| 6,730,118 B2 | 5/2004 | Spenser et al. | |
| 6,733,525 B2 | 5/2004 | Yang et al. | |
| 6,767,362 B2 | 7/2004 | Schreck | |
| 6,830,584 B1 | 12/2004 | Seguin | |
| 6,878,162 B2 | 4/2005 | Bales et al. | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,018,408 B2 | 3/2006 | Bailey et al. | |
| 7,166,126 B2 | 1/2007 | Spence et al. | |
| 7,276,078 B2 | 10/2007 | Spenser et al. | |
| 7,276,084 B2 | 10/2007 | Yang et al. | |
| 7,318,278 B2 | 1/2008 | Zhang et al. | |
| 7,335,213 B1 | 2/2008 | Hyde et al. | |
| 7,374,571 B2 | 5/2008 | Pease et al. | |
| 7,393,360 B2 | 7/2008 | Spenser et al. | |
| 7,462,191 B2 | 12/2008 | Spenser et al. | |
| 7,510,575 B2 | 3/2009 | Spenser et al. | |
| 7,585,321 B2 | 9/2009 | Cribier | |
| 7,618,446 B2 | 11/2009 | Andersen et al. | |
| 7,655,034 B2 | 2/2010 | Mitchell et al. | |
| 7,785,366 B2 | 8/2010 | Maurer et al. | |
| 7,959,672 B2 | 6/2011 | Salahieh et al. | |
| 7,993,394 B2 | 8/2011 | Hariton et al. | |
| 8,029,556 B2 | 10/2011 | Rowe | |
| 8,167,932 B2 | 5/2012 | Bourang | |
| 8,216,230 B2 | 7/2012 | Hauck et al. | |
| 8,449,606 B2 | 5/2013 | Eliasen et al. | |
| 8,597,348 B2 | 12/2013 | Rowe et al. | |
| 9,095,434 B2 | 8/2015 | Rowe | |
| 9,119,718 B2 | 9/2015 | Keranen | |
| 9,237,886 B2 | 1/2016 | Seguin et al. | |
| 9,364,326 B2 | 6/2016 | Yaron | |
| 9,463,268 B2 | 10/2016 | Spence | |
| 9,474,599 B2 | 10/2016 | Keranen | |
| 9,597,205 B2 | 3/2017 | Tuval | |
| 9,622,863 B2 | 4/2017 | Karapetian et al. | |
| 2002/0026094 A1 | 2/2002 | Roth | |
| 2002/0032481 A1 | 3/2002 | Gabbay | |
| 2002/0107535 A1 | 8/2002 | Wei et al. | |
| 2002/0138135 A1 | 9/2002 | Duerig et al. | |
| 2003/0050694 A1 | 3/2003 | Yang et al. | |
| 2003/0100939 A1 | 5/2003 | Yodfat et al. | |
| 2003/0158597 A1 | 8/2003 | Quiachon et al. | |
| 2003/0212454 A1 | 11/2003 | Scott et al. | |
| 2003/0225420 A1 | 12/2003 | Wardle | |
| 2003/0233142 A1* | 12/2003 | Morales ............ | A61B 17/0644 623/2.37 |
| 2004/0111006 A1 | 6/2004 | Alferness et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0096736 A1 | 5/2005 | Osse et al. | |
| 2005/0119682 A1 | 6/2005 | Nguyen et al. | |
| 2005/0119735 A1 | 6/2005 | Spence et al. | |
| 2005/0137691 A1 | 6/2005 | Salahieh et al. | |
| 2005/0137700 A1* | 6/2005 | Spence ............ | A61B 17/0482 623/2.36 |
| 2005/0182486 A1 | 8/2005 | Gabbay | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0025857 A1 | 2/2006 | Bergheim et al. | |
| 2006/0058872 A1 | 3/2006 | Salahieh et al. | |
| 2006/0149350 A1 | 7/2006 | Patel et al. | |
| 2007/0005131 A1 | 1/2007 | Taylor | |
| 2007/0010877 A1 | 1/2007 | Salahieh et al. | |
| 2007/0112422 A1 | 5/2007 | Dehdashtian | |
| 2007/0203503 A1 | 8/2007 | Salahieh et al. | |
| 2007/0203575 A1 | 8/2007 | Forster et al. | |
| 2007/0265700 A1 | 11/2007 | Eliasen et al. | |
| 2007/0293808 A1 | 12/2007 | Williams et al. | |
| 2008/0033542 A1 | 2/2008 | Antorisson et al. | |
| 2008/0077235 A1 | 3/2008 | Kirson | |
| 2008/0114442 A1 | 5/2008 | Mitchell et al. | |
| 2008/0125853 A1 | 5/2008 | Bailey et al. | |
| 2008/0208330 A1 | 8/2008 | Keranen | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0319037 A1 | 12/2009 | Rowe et al. | |
| 2010/0049313 A1 | 2/2010 | Alon et al. | |
| 2010/0145440 A1 | 6/2010 | Keranen | |
| 2010/0198347 A1 | 8/2010 | Zakay et al. | |
| 2010/0312333 A1 | 12/2010 | Navia et al. | |
| 2010/0318184 A1 | 12/2010 | Spence | |
| 2011/0015729 A1 | 1/2011 | Jimenez et al. | |
| 2012/0059458 A1 | 3/2012 | Buchbinder et al. | |
| 2012/0123529 A1 | 5/2012 | Levi et al. | |
| 2012/0283820 A1 | 11/2012 | Tseng et al. | |
| 2013/0023985 A1 | 1/2013 | Khairkhahan et al. | |
| 2013/0317598 A1 | 11/2013 | Rowe et al. | |
| 2014/0074299 A1 | 3/2014 | Endou et al. | |
| 2014/0081394 A1 | 3/2014 | Keranen et al. | |
| 2014/0114404 A1 | 4/2014 | Gammie et al. | |
| 2014/0172070 A1 | 6/2014 | Seguin | |
| 2014/0358222 A1 | 12/2014 | Gorman, III et al. | |
| 2014/0379074 A1 | 12/2014 | Spence et al. | |
| 2015/0230921 A1 | 8/2015 | Chau et al. | |
| 2015/0245910 A1 | 9/2015 | Righini et al. | |
| 2015/0282931 A1 | 10/2015 | Brunnett et al. | |
| 2015/0335428 A1 | 11/2015 | Keranen | |
| 2015/0335430 A1 | 11/2015 | Loulmet et al. | |
| 2015/0374493 A1 | 12/2015 | Yaron et al. | |
| 2016/0074165 A1 | 3/2016 | Spence et al. | |
| 2016/0095705 A1 | 4/2016 | Keranen et al. | |
| 2016/0184095 A1 | 6/2016 | Spence et al. | |
| 2016/0199177 A1 | 7/2016 | Spence et al. | |

(56) References Cited

U.S. PATENT DOCUMENTS

| | | |
|---|---|---|
| 2016/0256276 A1 | 9/2016 | Yaron |
| 2016/0346080 A1 | 12/2016 | Righini et al. |
| 2017/0007399 A1 | 1/2017 | Keranen |
| 2017/0007402 A1 | 1/2017 | Zerkowski et al. |
| 2017/0217385 A1 | 8/2017 | Rinkleff et al. |
| 2017/0266005 A1 | 9/2017 | McGuckin, Jr. |
| 2017/0273788 A1 | 9/2017 | O'Carroll et al. |
| 2018/0206074 A1 | 7/2018 | Tanasa et al. |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| EP | 0103546 A1 | 3/1984 |
| EP | 0597967 A1 | 5/1994 |
| EP | 0592410 B1 | 10/1995 |
| EP | 0850607 A1 | 7/1998 |
| EP | 1432369 A1 | 6/2004 |
| EP | 1521550 A2 | 4/2005 |
| EP | 1796597 A2 | 6/2007 |
| EP | 1296618 B1 | 1/2008 |
| EP | 1827314 B1 | 12/2010 |
| EP | 2620125 A1 | 7/2013 |
| EP | 2726018 A2 | 5/2014 |
| EP | 2806829 A2 | 12/2014 |
| FR | 2788217 A1 | 7/2000 |
| FR | 2815844 A1 | 5/2002 |
| SU | 1271508 A1 | 11/1986 |
| WO | 9117720 A1 | 11/1991 |
| WO | 9301768 A1 | 2/1993 |
| WO | 9829057 A1 | 7/1998 |
| WO | 9940964 A1 | 8/1999 |
| WO | 9947075 A1 | 9/1999 |
| WO | 0041652 A1 | 7/2000 |
| WO | 0149213 A2 | 7/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 03028558 A2 | 4/2003 |
| WO | 03047468 A1 | 6/2003 |
| WO | 2005034812 A1 | 4/2005 |
| WO | 2005084595 A1 | 9/2005 |
| WO | 2006011127 A2 | 2/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008091515 A2 | 7/2008 |
| WO | 2009033469 A1 | 3/2009 |
| WO | 2009155561 A2 | 12/2009 |
| WO | 2010121076 A2 | 10/2010 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |
| WO | 2017103833 A1 | 6/2017 |

OTHER PUBLICATIONS

H.R. Andersen "History of Percutaneous Aortic Valve Prosthesis," Herz No. 34, pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311, 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

\* cited by examiner

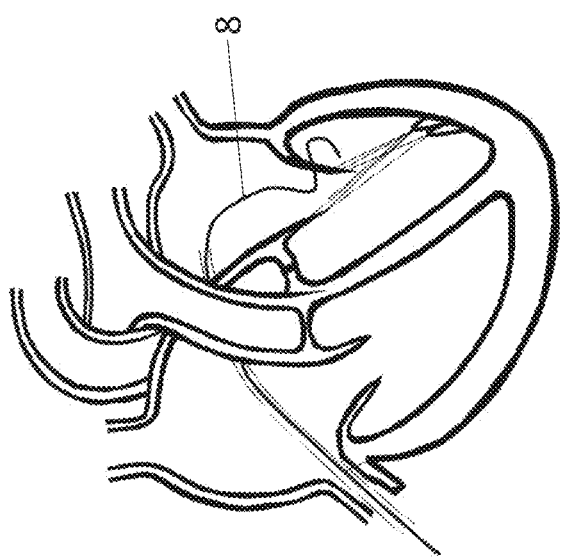

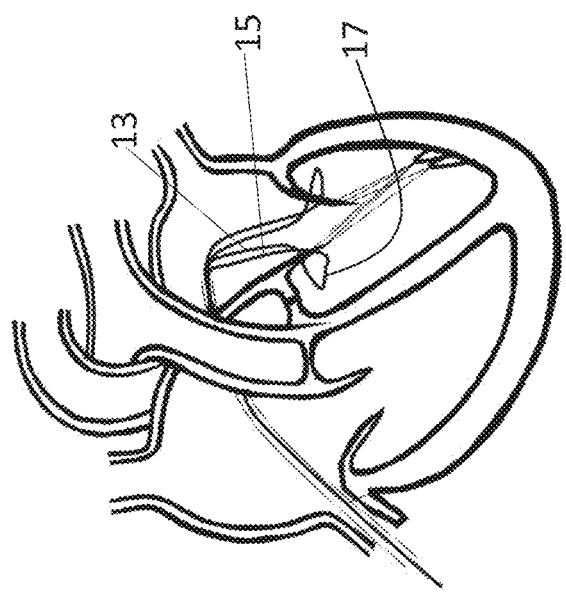

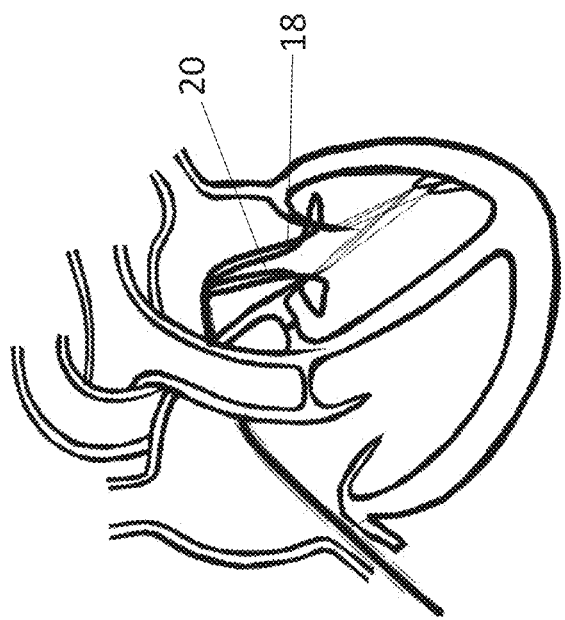

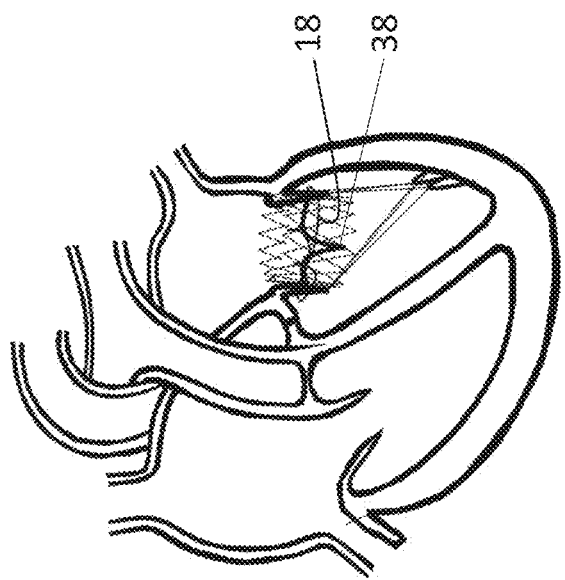

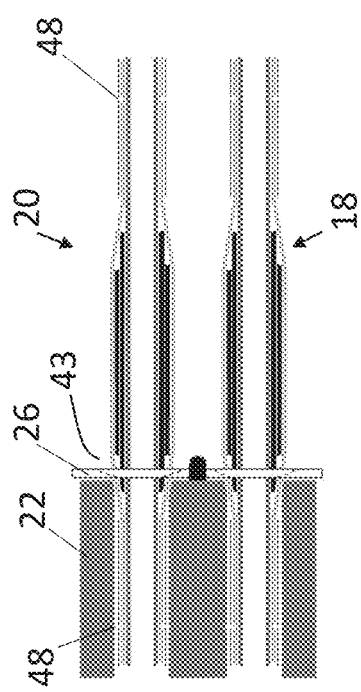

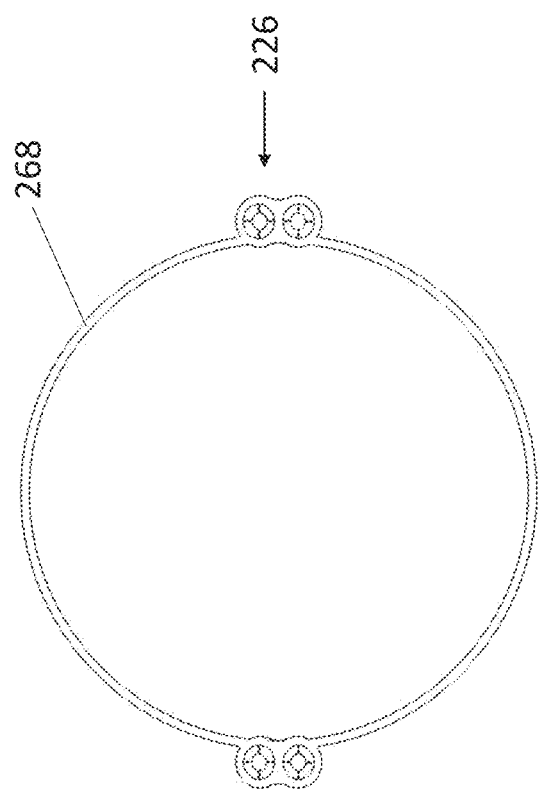

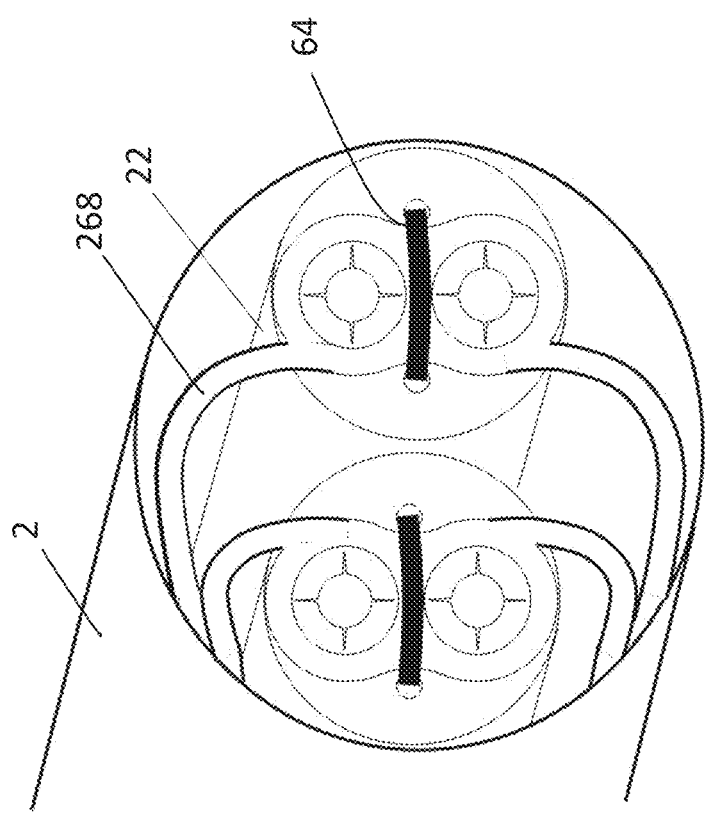

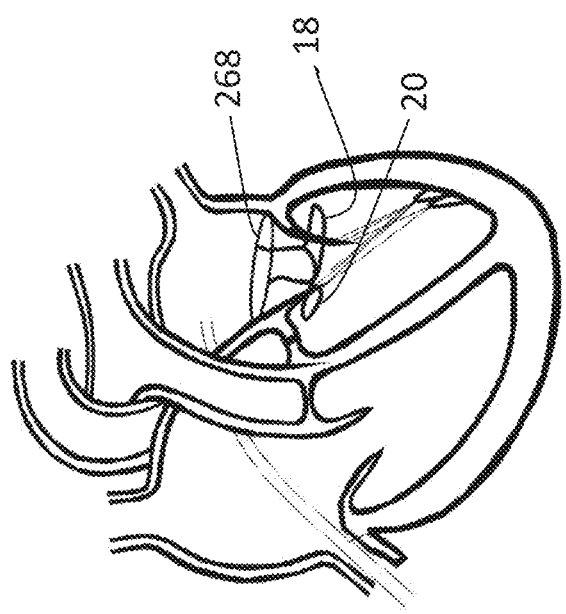

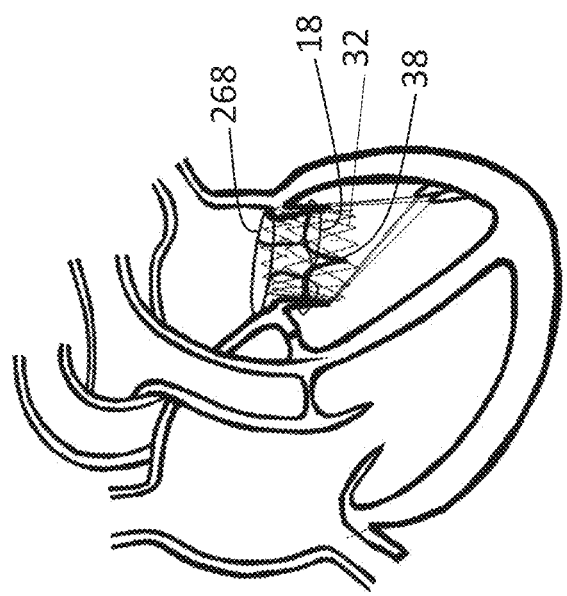

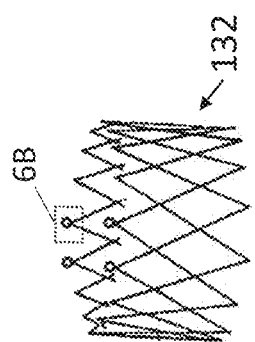

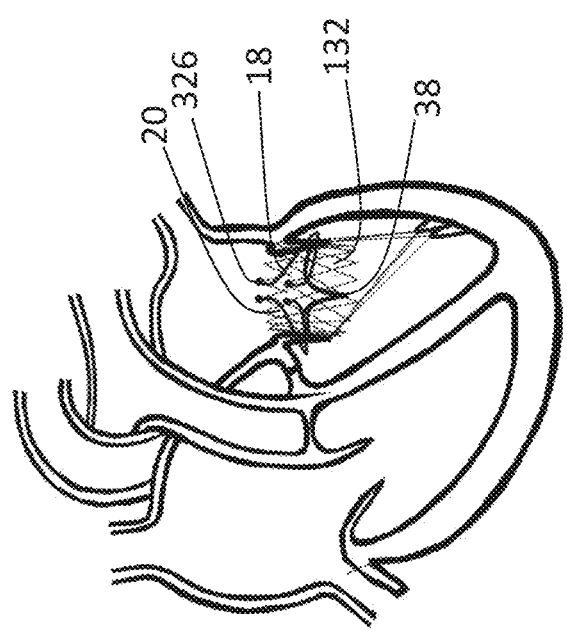

LOW PROFILE TRANSSEPTAL CATHETER AND IMPLANT SYSTEM FOR MINIMALLY INVASIVE VALVE PROCEDURE

CROSS-REFERENCE TO RELATED APPLICATIONS

This application is a divisional of U.S. patent application Ser. No. 15/018,781, filed on Feb. 8, 2016, which claims the benefit of U.S. Provisional Application No. 62/113,839 filed on Feb. 9, 2015, both of which applications are incorporated herein by reference in their entirety.

FIELD OF THE INVENTION

The present application is related to the field of interventional cardiology systems and procedures and, in particular, systems and procedures for heart valve repair.

BACKGROUND

Prosthetic devices are commonly used to replace or repair native heart valves that have become inefficient due to age, disease, or congenital reasons. Valve insufficiency, for example, is characterized by a loose or elastic valve structure. This often results in regurgitation wherein the valve leaflets fail to close property ("coapt") and guard against backflow of blood.

Transvascular techniques have enabled physicians to access the mitral and other valves for repair without open-heart surgery. Valves or annuloplasty rings may be delivered to the site of the valve by catheter and expanded once properly positioned.

A physician may have difficulty precisely positioning prosthetic devices between the mitral valve leaflets—especially when the mitral valve is insufficient. The prosthetic devices may slip upon expansion within the relatively elastic annulus of the insufficient mitral valve.

A physician may provide support for the annular ring of the valve during implantation to compensate for mitral valve insufficiency. But, positioning of such support devices in a safe and minimally invasive manner is technically challenging. For example, the chordae tendinae attached to the mitral valve leaflets can interfere with efforts to support the valve or its annulus.

It is therefore desirable to provide improved systems and methods for supporting replacement valves, especially replacement valves implanted with minimally invasive procedures.

SUMMARY

Disclosed herein are methods and apparatuses for greatly simplifying and improving the outcome of minimally invasive valve procedures—making those procedures much more accessible to less experienced physicians or cardiologists. For example, implementations are applicable to full mitral valve replacement, or to mitral valve annuloplasty. The mitral valve can be accessed by femoral catheterization with a fluoroscopically guided, low-profile catheter. Once the right atrium is accessed and the interatrial septum is punctured, the mitral valve can be approached from the left atrium. This approach avoids contact with the left ventricular outflow tract and the chordae tendineae.

As part of the method, two leaflet braces circumnavigate the anterior and posterior mitral valve leaflets, forming a loop around each leaflet. Tension in the atrial direction from the catheter keeps the loops tightly wedged under the leaflets for the remainder of the procedure. A fastener joins the ends of each loop to form one annular ring circling the valve under the anterior and posterior leaflets.

In some implementations, the procedure can be performed with a sub-commissural catheter to assist in steering behind the leaflets. After bracing the individual leaflets, a transcatheter heart valve system can then be deployed between the native leaflets. Expansion of the heart valve traps and sandwiches the native mitral valve leaflets between the valve frame and the leaflet braces. The procedure can be performed in catheterization laboratories and by practitioners with varying levels of expertise.

A method of supporting a heart valve is provided in one implementation. The method includes looping around a first leaflet of the heart valve. And, applying tension directed through the valve to the first leaflet. The method also includes performing a procedure on the heart valve.

The method can further comprise looping around a second leaflet of the heart valve and applying tension directed through the valve to the second leaflet.

The method can also include extending a guide catheter through the valve and advancing a first guide wire through the guide catheter. In this manner, looping around the leaflet includes extending the first guide wire around the first leaflet. Also, a second guide wire could be deployed through the guide catheter and looped around the second leaflet.

The guide wires can include snare loops and the method includes snaring the snare loop of the guide wires after extending them around the leaflets.

The method can also include forming first and second leaflet braces. A first leaflet brace extends over the first guide wire and around the first leaflet. Also, a second leaflet brace is extended over the second guide wire and around the second leaflet.

The method can also include securing adjacent ends of the leaflet braces to each other to form a closed circle. For example, the physician can attach a first pair of adjacent ends using a first leaflet brace and a second pair of adjacent ends using a second leaflet brace. Then, as an exemplary procedure on the heart valve, a replacement heart valve can be expanded within the native heart valve. Expansion for example can include releasing a self-expanding heart valve within the (native) heart valve and against the leaflets (directly) and the leaflet braces (indirectly). The method can also include removing excess tubing from the leaflet braces.

Advantageously, all of these procedures can occur while the method applies tension to the leaflets for improved results. For example, the tension on the leaflets helps with accurate positioning (and slip avoidance) during expansion of the replacement heart valve.

The heart valve can be, for example, a mitral heart valve and the method can be used to avoid and preserve the chordae tendinae. Other heart valves might be aortic, tricuspid or pulmonic, or prior replacement heart valves in need of repair.

In another implementation, a system is disclosed for supporting a heart valve having at least two leaflets. The system can include at least one fastening catheter and at least one leaflet brace. The fastening catheter has a distal end and defines at least two adjacent lumens extending through the distal end. The fastening catheter also includes at least one fastener coupled to the fastening catheter, such as at the distal end. The leaflet brace has an elongate flexible structure configured to extend through one of the lumens of the fastening catheter and around at least one leaflet of the heart valve.

The elongate flexible structure can include an abutment surface configured to stop advancement of the fastener over the leaflet brace. The elongate flexible structure can also include an inner elastic layer and an outer functional layer. The outer functional layer can be, for example, an ingrowth layer, a radiopaque or a shrink layer. The elongate flexible structure can also include a shortening mechanism, such as a tear notch defined within the elongate flexible structure.

The system may include a first and second leaflet braces and first and second fastening catheters. A first pair of adjacent ends of the first and second leaflet braces are configured to extend through adjacent lumens of the first fastening catheter. A second pair of adjacent ends of the first and second leaflet braces are configured to extend through adjacent lumens of the second fastening catheter. The fastener of the first fastening catheter is configured to attach together the first pair of adjacent ends. The fastener of the second fastening catheter is configured to attach together the second pair of adjacent ends, thus forming an annular ring encircling the at least one leaflet of the heart valve.

The fastener can define a pair of adjacent openings configured to align over the two adjacent lumens at the distal end and receive therethrough at least a portion of the leaflet brace. The fastener can also include a plurality of locking tabs extending around the adjacent openings.

The system can also include a fastener hoop having coupled thereto the fastener of the first fastening catheter and the fastener of the second fastening catheter. The fastener hoop can be circular with the fasteners coupled on the opposite sides of the hoop.

The system can also include a transseptal introducer sheath configured to deliver the at least one fastening catheter.

The system can also include one or more barbs coupled to the at least one leaflet brace to help secure the brace to heart tissue.

The system can also include a prosthetic valve configured to expand within the leaflets of the heart valve and the least one leaflet brace. The expanded prosthetic valve can sandwich the leaflets between the prosthetic valve and the at least one leaflet brace.

The system can include an elongate coupling member (such as a suture) releasably coupling the fastener to the at least one fastening catheter.

DESCRIPTION OF DRAWINGS

FIG. 1B is a cross-sectional schematic of the heart from FIG. 1A with introduction of a guide catheter.

FIG. 1E is a cross-sectional schematic of the heart from FIG. 1A with introduction of a second snare catheter and formation of a loop around the anterior leaflet.

FIG. 1F is a cross-sectional schematic of the heart from FIG. 1A with introduction of first and second leaflet braces over the loops.

FIG. 1I is a cross-sectional schematic of the heart from FIG. 1A after completion of the procedure.

FIG. 3C shows a cross-section of the fastening catheter and fastener of FIG. 3A after advancement of the fastening catheter down the leaflet brace.

FIG. 5A shows a top view of two fasteners mounted on a fastener hoop.

FIG. 5B shows a perspective view of the fasteners and fastener hoop of FIG. 5A in a transseptal introducer sheath.

FIG. 5D is a cross-sectional schematic of the heart after expansion of the fastening hoop of FIG. 5C.

FIG. 5F is a cross-sectional schematic of the heart after completion of the procedure using the fastening hoop of FIGS. 5A-5D.

FIG. 6A is perspective view of a fastener stent.

FIG. 6C is a cross-sectional schematic of a heart after undergoing a minimally invasive mitral valve procedure with the fastener stent of FIG. 6A.

FIG. 7O is a cross-sectional schematic of the heart of FIG. 7E-7N after completion of a minimally invasive mitral valve procedure with the sub-commissural catheter and transseptal introducer sheath of FIG. 7A-D.

DETAILED DESCRIPTION

Figure 1A:
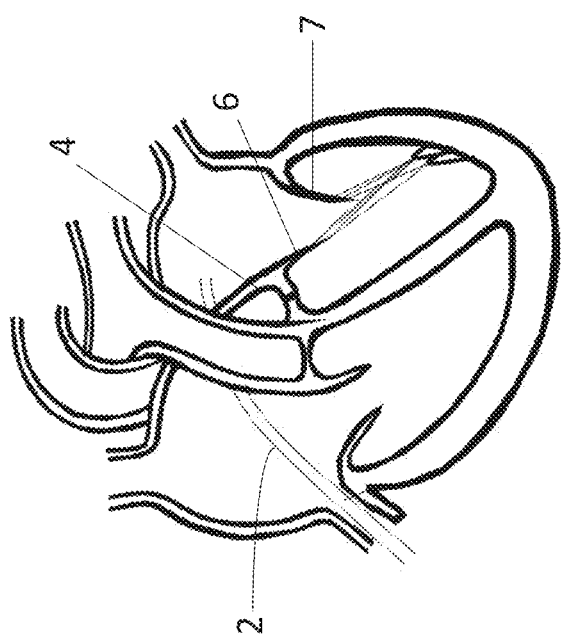
FIG. 1A is a cross-sectional schematic of a heart undergoing a minimally invasive mitral valve procedure including introduction of a catheter via a transseptal access point.

The following description of certain examples of a medical system (e.g., catheters and implants) should not be used to limit the scope of the medical system. Other examples, features, aspects, embodiments, and advantages of the medical system will become apparent to those skilled in the art from the following description. As will be realized, the medical system is capable of additional aspects, all without departing from the spirit of the medical apparatus. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, can be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Apparatuses and methods for performing minimally invasive mitral valve procedures are disclosed herein. For example, these apparatuses and methods can be applied to full mitral valve replacement, or to mitral valve annuloplasty. Although particularly suited for mitral valves, these apparatuses and methods can also be applied to other valves. The procedures can be performed in catheterization laboratories and by practitioners with varying levels of expertise.

For illustrative purposes, certain embodiments of the system are described as being used in connection with a trans-catheter heart valve (THV). For example, the systems and methods may be employed with the balloon-expandable THV described in U.S. Pat. No. 8,764,820, which is hereby expressly incorporated herein by reference. It should be understood, however, that the systems and methods should not be limited to use with balloon-expandable THVs. Instead, embodiments of the disclosed systems and methods can be used to secure a wide variety of THVs delivered through a variety of mechanisms (e.g., self-expanding heart valves, mechanically-expanding heart valves, other balloon-expanding heart valves, and the like). For instance, any of the embodiments described in U.S. Pat. No. 6,730,118 can be used with embodiments of the disclosed system. U.S. Pat. No. 6,730,118 is hereby expressly incorporated herein by reference.

Access to the mitral valve can be obtained using femoral catheterization with a fluoroscopically guided, low-profile catheter. For example, the right atrium is accessed and the interatrial septum punctured to get to the left atrium. Then the mitral valve is approached through the left atrium. Advantageously, this approach avoids contact with the left ventricular outflow tract and the chordae tendineae.

Two leaflet braces are extended over guide wires to form semicircular loops that circumnavigate the anterior and posterior mitral valve leaflets. Tension is applied to the catheter from the atrial direction to keep the leaflet braces tightly wedged under the leaflets for the remainder of the procedure. A fastener joins the ends of each loop to create one annular ring encircling the valve under the anterior and posterior leaflets.

In some implementations, the procedure can be performed with a sub-commissural catheter to assist in steering behind the leaflets. In certain implementations, the remaining catheters can be separated from the leaflet braces after implantation, leaving the annular ring in place behind the leaflets. The annular ring formed can serve as part of an annuloplasty device. Alternatively, a transcatheter heart valve system can then be deployed between the native leaflets. Expansion of the heart valve traps and sandwiches the native mitral valve leaflets between the valve frame and the leaflet braces.

To begin the transseptal procedure, a physician punctures the septum with a needle and advances a guide wire through the needle. The physician then retrieves the needle, leaving a guide wire across the septum. The physician then advances a dilator with a cone shaped distal end over the guide wire and across the septum. The physician then advances a transseptal introducer sheath 2 over the dilator, through the interatrial septum 4 and toward the anterior and posterior leaflets 6, 7 of a mitral valve as seen in FIG. 1A.

Figure 1C:
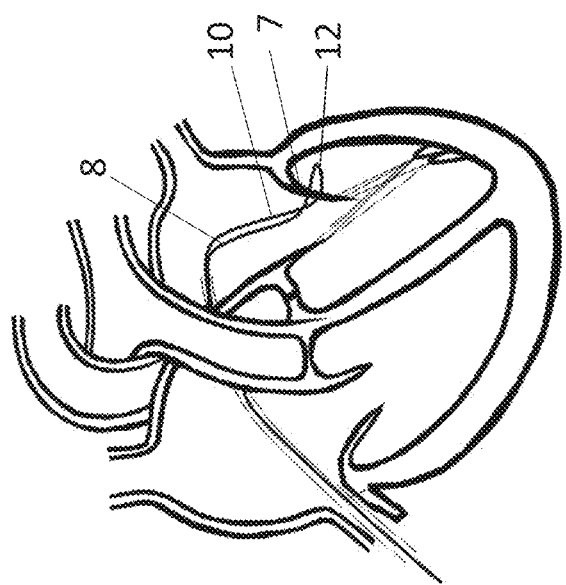
FIG. 1C is a cross-sectional schematic of the heart from FIG. 1A with introduction of a snare catheter and formation of a loop around the posterior leaflet.

As in FIG. 1B, a first double bend guide catheter 8 extends from the introducer sheath 2 to cannulate the mitral valve at the posteromedial commissure. The physician then advances a first guide wire with a ringed end through guide catheter 8 and around the posterior leaflet 7 towards the anterolateral commissure. A first snare catheter 10 then cannulates the mitral valve at the anterolateral commissure. A first snare guide wire positioned at the distal end of the snare catheter 10 captures the first ringed guide wire and pulls it out, so that the guide wire circumvents the posterior leaflet 7 at the base of the mitral valve, as in FIG. 1C. This forms a posterior leaflet wire loop 12.

Figure 1D:
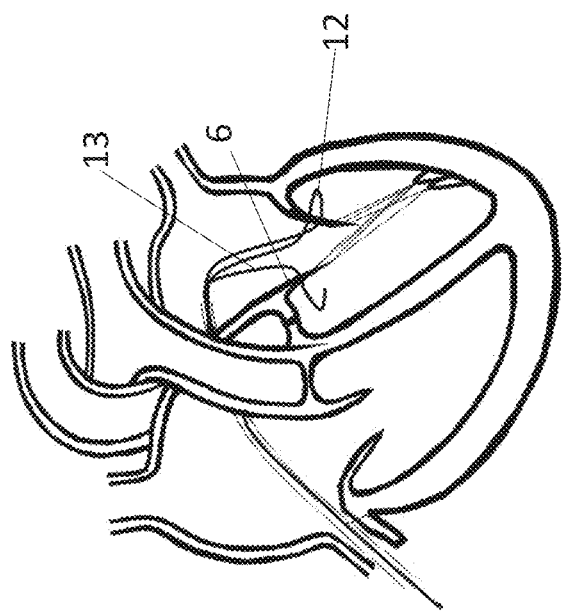
FIG. 1D is a cross-sectional schematic of the heart from FIG. 1A with introduction of a second guide catheter.

The process is repeated in FIGS. 1D and 1E around the anterior leaflet 6 using a second double bend guide catheter 13, a second ringed guide wire (not shown), a second snare catheter 15, and a second snare guide wire (not shown). This forms an anterior leaflet wire loop 17.

Figure 2:
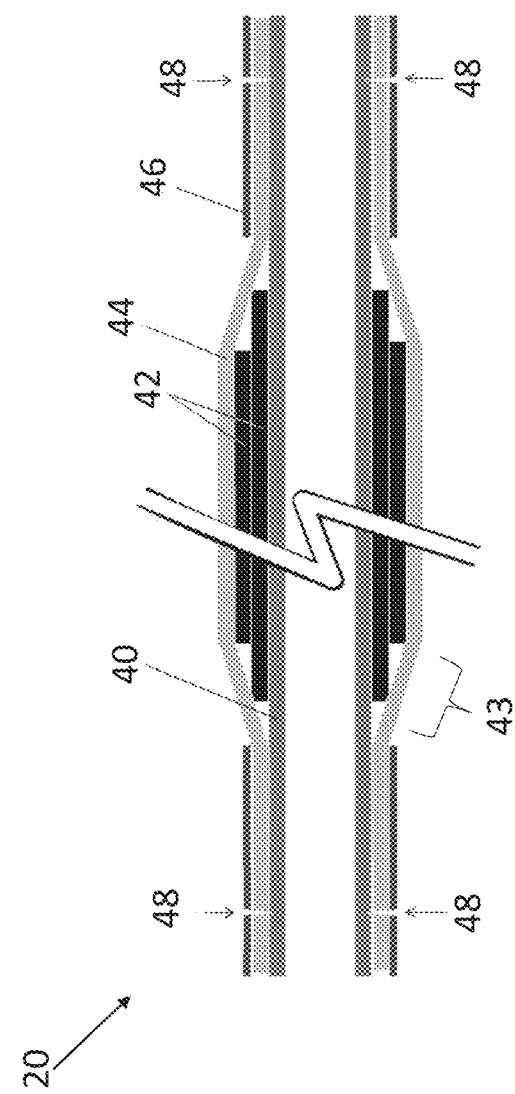
FIG. 2 shows a cross-section of a leaflet brace.

The physician retracts the guide and snare catheters, leaving the wire loops in place. The physician then slides two tubular leaflet braces 18, 20 over the loops such that they are positioned around the posterior and anterior wire leaflet loops 12, 17 as seen in FIG. 1F. The structure of the braces is shown in FIG. 2 and will be described in greater detail below.

Figure 1G:
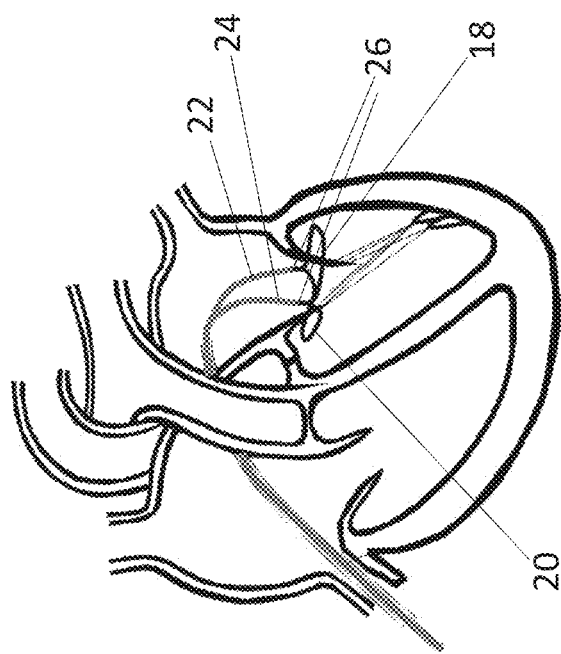
FIG. 1G is a cross-sectional schematic of the heart from FIG. 1A with introduction of fastening catheters to secure the loops at either end.

The physician then slides anterolateral and a posteromedial fastening catheters 22, 24 along the guide wires and over portions of the leaflet braces 18, 20 as seen in FIG. 1G. In particular, the posteromedial fastening catheter 22 runs up the two ringed guide wires 9, 14 and over the leaflet brace ends located at the posteromedial side of the valve. The anterolateral fastening catheter 24 runs up the two snared guide wires 11, 15 and over the brace ends located at the anterolateral side of the valve.

Fasteners 26 located at the distal faces of the fastening catheters 22, 24 are used to join the two leaflet braces at both commissures. Examples of fastener structures are shown in FIGS. 3A, 4A, 5A, and 6A, and are described in greater detail below.

The physician then removes excess tubing from the leaflet braces and retracts the excess tubing back through the transseptal introducer sheath 2. The two braces now form one annular ring circling the valve under the anterior and posterior leaflets 6, 7, as shown in FIG. 1G. Both fastening catheters 22, 24 are kept under tension, which holds the annular ring close to the base of the mitral valve.

Figure 1H:
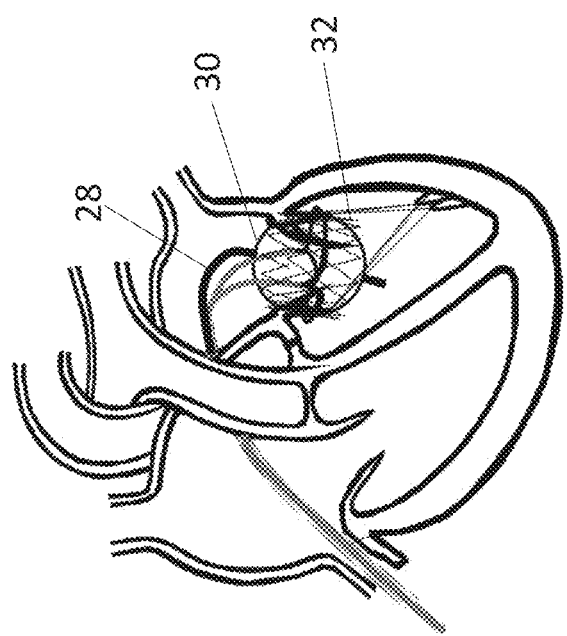
FIG. 1H is a cross-sectional schematic of the heart from FIG. 1A after introduction and expansion of a balloon inflatable stented heart valve within the native mitral valve.

The physician can then guide a valve delivery catheter 28 through the transseptal introducer sheath 2 and into the space between mitral valve leaflets 6, 7. The transcatheter heart valve 38 can be mounted on a stent 32. It can be self-expandable, mechanically-expandable, or expanded by balloon 30 as shown in FIG. 1H. Expansion of the heart valve 38 traps and sandwiches the native mitral valve leaflets 6, 7 between the valve frame and the leaflet braces 18, 20. The physician then releases fasteners 26 from the fastening catheters 22, 24 by removing a suture 64 that binds them to the fastening catheter (see FIGS. 3A-3E). The physician then retracts the fastening catheters and balloon delivery catheter 28 back through the transseptal introducer sheath. Finally, the transseptal introducer sheath 2 is removed from the patient. FIG. 1I shows the heart after the procedure with the surgical devices in place.

As shown in FIG. 2, stacked layers of polymer tubing form the exemplary leaflet braces 18, 20. The leaflet braces 18, 20 can be formed using standard catheter extrusion and braiding techniques. In this implementation, the innermost tubing 40 can be made from an elastic polymer such as PTFE or PU, or other elastic polymers suitable for medical device tubing. The innermost tubing 40 can have 10-100% elongation at failure. For example, the innermost tubing 40 can have about 20% elongation at failure.

Two or more layers of radiopaque marker tubing 42 extend over a portion of the innermost tubing 40 of the leaflet braces seen in FIG. 2. These layers widen the diameter of the leaflet brace 18, 20 to form an abutment 43 along with tubing 44. Abutment 43 stops the fastening catheter 22, 24 from moving further along the leaflet brace during the fastening step. The radiopaque marker tubing 42 also allows practitioners to more easily fluoroscopically monitor the position of the leaflet braces as they are arranged behind the anterior and posterior leaflets 6, 7.

As shown in FIG. 2, one or more layers of tissue ingrowth tubing 44 can cover the radiopaque marker tubing 42 of the leaflet braces 18, 20. The tissue ingrowth tubing 44 extends in both directions past the radiopaque marker tubing 42. It can be a porous or filamentous material that encourages fixation of the leaflet brace to the tissue behind the leaflets. For example, the tissue ingrowth tubing 44 can be a multifilament PTFE yarn.

The leaflet braces 18, 20 can have a shortening mechanism to allow removal of excess tubing during the mitral valve procedure. For example, tear notches 48 can be provided as seen FIG. 2. These tear notches 48 create weak points that allow excess tubing to be pulled off of the leaflet braces and slid back up the transseptal introducer sheath 2. Shrink tubing 46 can extend over the tissue ingrowth tubing 44 anywhere that tissue ingrowth is not desired. This can, for example, prevent the yarn from fraying after the ends are torn.

FIGS. 3A-3E depict the structural details of exemplary fastening catheters 22, fasteners 26, and the process of fastening the leaflet braces 18, 20. The exemplary fastener 26 depicted in FIG. 3A has an elongate fastener body 50 with rounded ends, two locking tab rings 54 positioned inward from the edge of the fastener body, and locking tabs 56 arranged circumferentially inside each locking tab ring 54 and defining spaces through which the leaflet braces 18, 20 can move. The locking tabs taper slightly as they extend inward and away from the fastener body 50. In the implementation depicted in FIG. 3A, there are 4 locking tabs per locking tab ring. However, the fasteners 26 can have fewer—such as 2—locking tabs or more—such as 16—locking tabs. Alternatively, the fasteners can secure the leaflet braces 18, 20 using other mechanisms, such as screws, clips, latches or knots. The fastener 26 can be cut from sheet metal with a laser or other cutting techniques. In some implementations, the fastener 26 can be a shape-memory metal, such as Nitinol. In other implementations, the fastener 26 can be stainless steel or other metals acceptable for use in implantable medical devices.

Figure 3A:
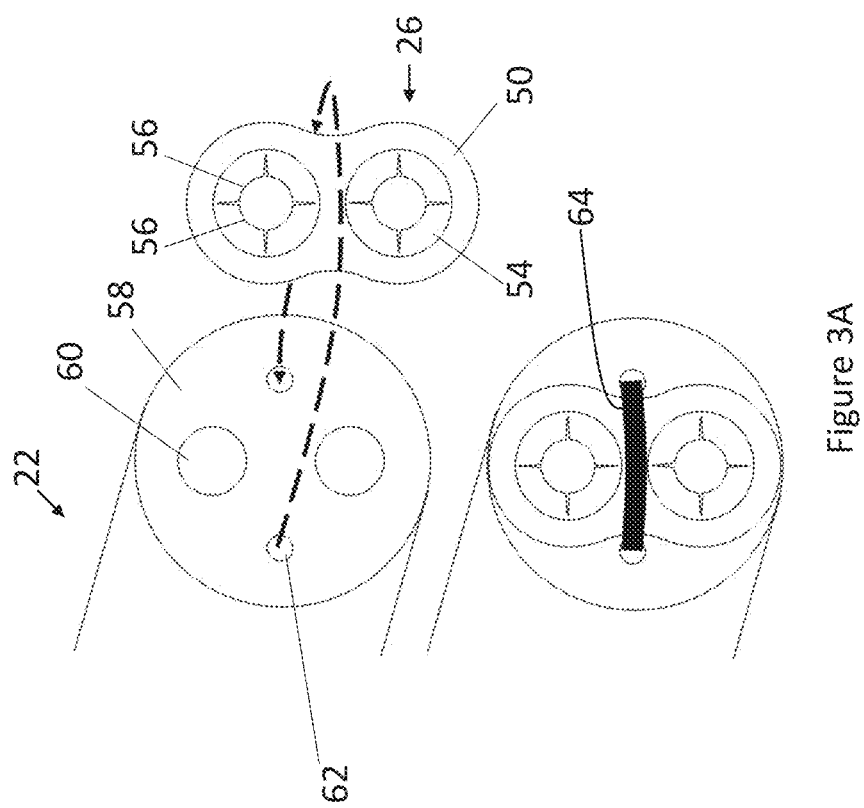
FIG. 3A shows a perspective view of a distal end of a pair of fastening catheters.
Figure 3B:
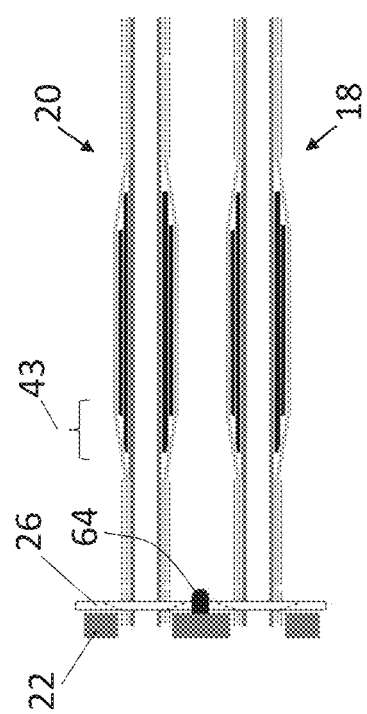
FIGS. 3B and 3F show a cross section and perspective view of the fastening catheter and fastener of FIG. 3A engaged with a leaflet brace.
Figure 3D:
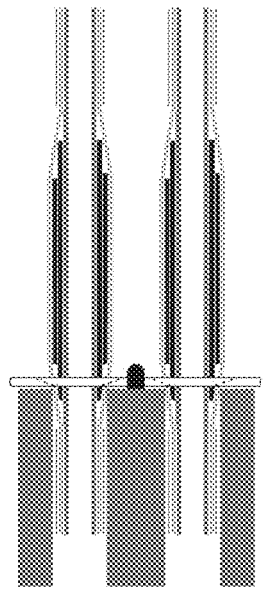
FIG. 3D shows a cross-section of the fastening catheter, fastener and leaflet brace of FIG. 3C after removal of the leaflet brace ends.

As shown in FIG. 3A, the body 50 of the fastener 26 can be secured to the distal face 58 of the fastening catheter 22 using suture 64. Fastening catheter lumens 60 slide down over the leaflet braces 18, 20, as shown in FIG. 3B. The fastening catheter 22 continues to push the fastener 26 along the leaflet braces 18, 20 until it reaches the abutment 43, as in FIG. 3C. Locking tabs 56 catch on the wider section of leaflet braces 18, 22 and prevent it from slipping backward. A practitioner can remove the excess tubing from the leaflet braces by pulling at the ends. The polymers tear at the tear notches 48, and the excess can be retracted back up the transseptal introducer sheath 2, as shown in FIG. 3D.

Figure 3E:
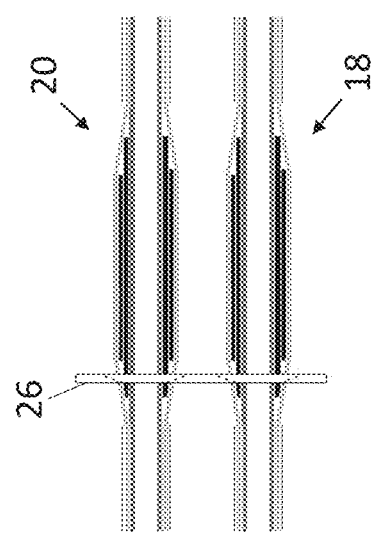
FIGS. 3E and 3G shows a cross-section and perspective view of the fastener and leaflet brace of FIGS. 3A-3D after removal of the fastening catheter.
Figure 3F:
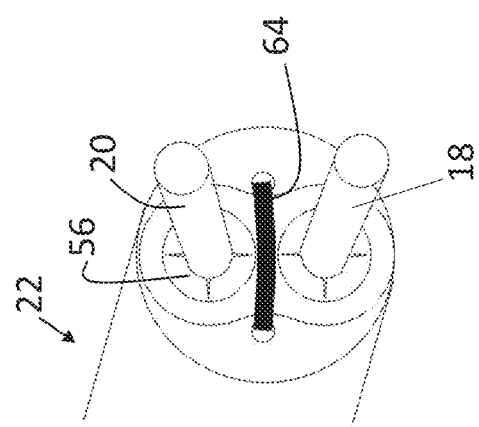
Figure 3G:
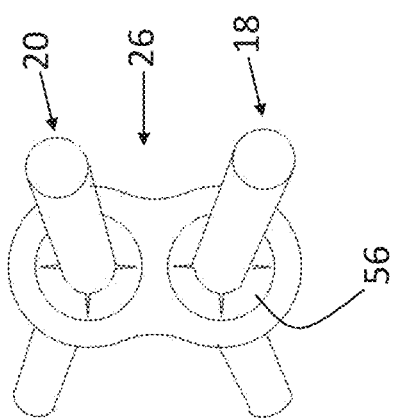

FIG. 3E shows the leaflet brace 20 after the fasteners are released and the fastening catheter is withdrawn. To release the fastener from the fastening catheter, the physician releases one end of the suture 64 and pulls on the other end. The suture slides over the fastener body 50 and back up the transseptal introducer sheath 2. This releases the fastener 26 and the attached leaflet braces 18, 20 from the fastening catheter 22. The fastening catheter 22 is then withdrawn up the transseptal introducer sheath 2.

The sheath 2 can be between 10-50 French, depending on the particular method being performed. For example, in the implementation depicted by FIGS. 1A-1I, the sheath 2 can contain both the fastening catheters and the valve delivery catheter simultaneously. In this case the introducer sheath 2 can be between 25-50 French. The implementation of FIGS. 4A-E allows for the fastening catheter to be removed prior to entry of the valve delivery catheter. Thus, the introducer sheath 2 of other implementations can be narrower because they do not have to house multiple catheters simultaneously.

Figure 4A:
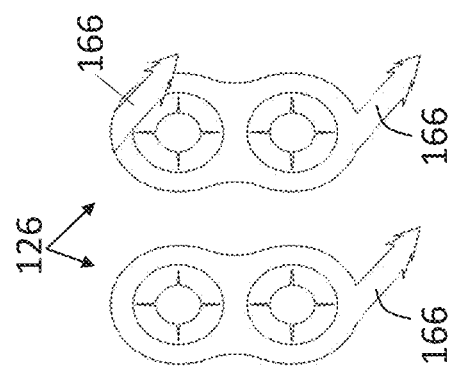
FIG. 4A shows a perspective view of two fasteners having barbs.
Figure 4B:
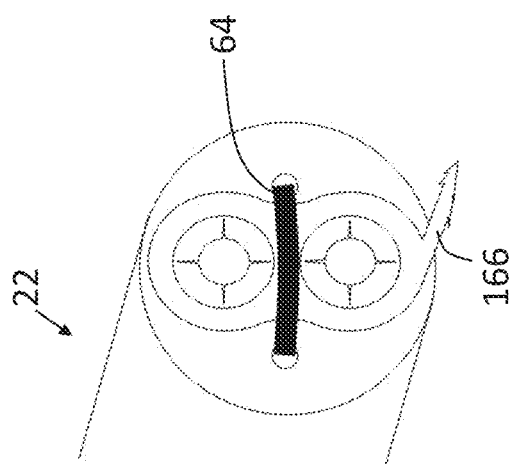
FIG. 4B shows a perspective view of one of the fasteners of FIG. 4A bound to a fastening catheter.
Figure 4C:
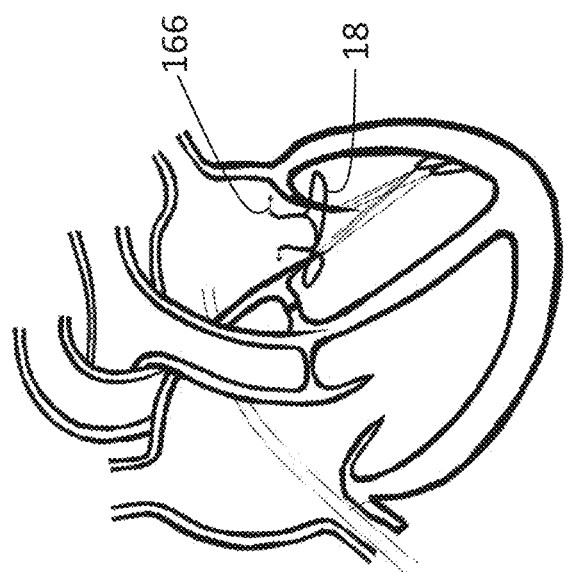
FIG. 4C is a cross-sectional schematic of a heart having a leaflet brace ring fastened by the fasteners of FIGS. 4A and 4B.

In the implementation depicted in FIGS. 4A-E, fasteners 126 can include one or more fastener barbs 166. FIG. 4A shows two exemplary fasteners 126 with barbs. FIG. 4B shows one of the exemplary fasteners 126 bound to a fastening catheter 22 by a suture 64. After removal of the fastening catheters 22, 24, the barbs protrude as shown in FIG. 4C. The physician can use a steerable catheter to push fastener barbs 166 into the myocardial wall, securing the annular ring formed by the leaflet braces 18, 20.

Figure 4D:
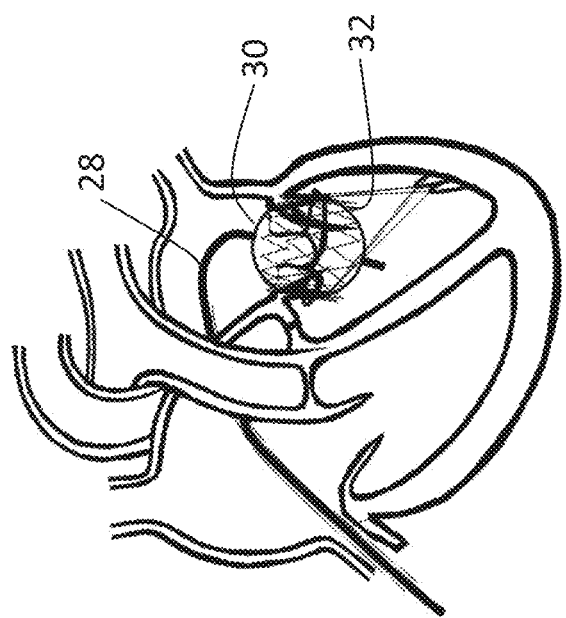
FIG. 4D is a cross-sectional schematic of the heart of FIG. 4C after expansion of a balloon inflatable stented heart valve within the native mitral valve.
Figure 4E:
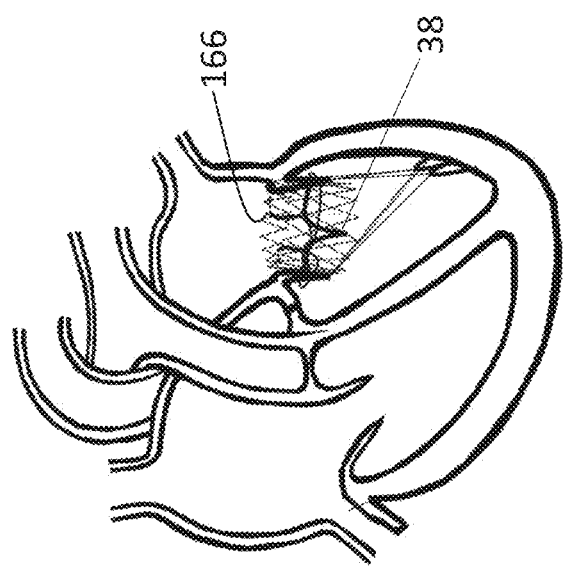
FIG. 4E is a cross-sectional schematic of a heart after completion of the procedure using the fasteners of FIGS. 4A-4B.

The physician can then deploy a transcatheter heart valve 38 via a valve delivery catheter 28. The expansion of the valve 38 secures barbs 166 within the myocardial tissue. FIG. 4D is a cross-sectional schematic of the heart of FIG. 4C after expansion of a balloon inflatable stented heart valve within the native mitral valve. FIG. 4E is a cross-sectional schematic of a heart after completion of the procedure using the fasteners of FIGS. 4A-4B. Because fastening catheters 22, 24 are removed prior to inserting the valve delivery catheter 28, the diameter of the transseptal introducer sheath 2 can be lower than for the implementation depicted in FIGS. 1A-1I. For example, the diameter of the transseptal introducer sheath can be between 10-30 French.

Figure 5C:
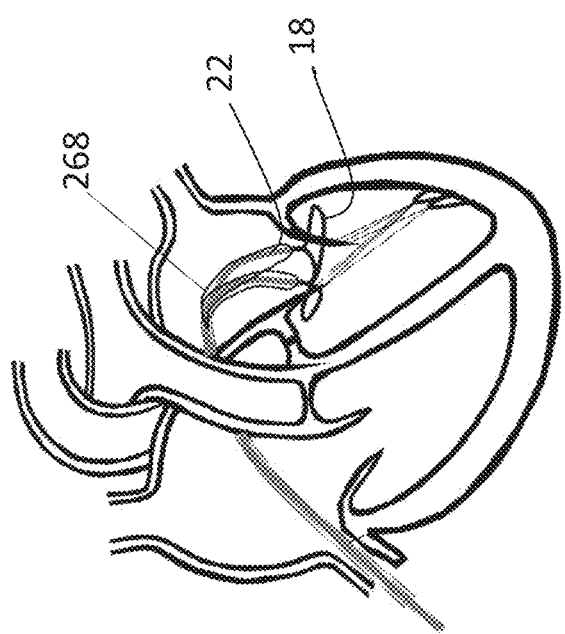
FIG. 5C is a cross-sectional schematic of the introduction of the fastening hoop of FIGS. 5A-5B during a mitral valve procedure.

In the implementation depicted in FIGS. 5A-5F, fasteners 226 are mounted on a flexible fastener hoop 268. The fastener hoop 268 can be between about 50-65 millimeters in diameter. The fasteners 226 and hoop 268 can be one piece, as shown in FIG. 5A, or they can be separate pieces joined after forming. The fastening hoop 268 can be made of a shape memory material. For example, the shape memory material can be Nitinol.

During deployment, the fasteners 226 are secured by suture 64 at the distal face 58 of the fastening catheter 22 as shown in FIG. 5B. The fastener hoop 268 is folded outside of the fastening catheters but within the transseptal introducer sheath 2.

FIG. 5C depicts the fastening catheters advanced along the leaflet braces 18, 20 with the ends of the fastening hoop 268 still retained in the folded state by the introducer sheath 2. Once the fastening catheters 22, 24 are sufficiently spaced from the distal end of the introducer sheath 2, the ends of the fastening hoop 268 open above the mitral valve while the fasteners 226 secure the ends of the leaflet braces 18, 20. The physician then releases the fastening hoop 268 and removes the fastening catheters 22, 24.

Figure 5E:
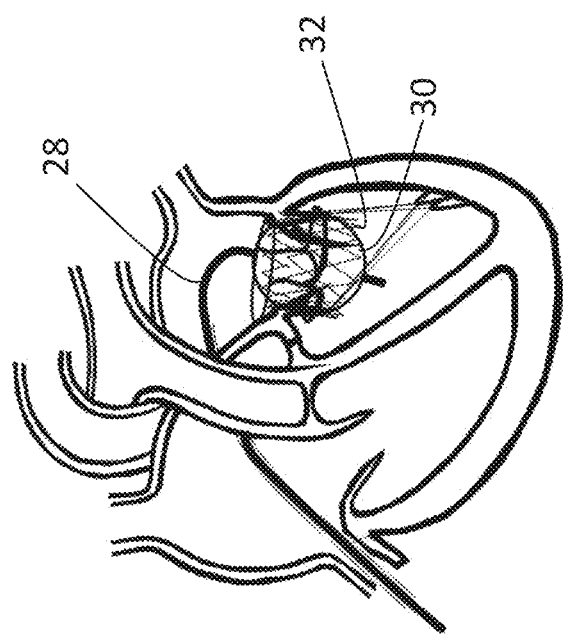
FIG. 5E is a cross-sectional schematic of the heart of FIG. 5D after expansion of a balloon inflatable stented heart valve within the native mitral valve.

FIG. 5D shows the fastening hoop 268 in an open position above the mitral valve, while the leaflet braces 18, 20 form an annular ring below the mitral valve. The combination of the fastener hoop 268 and the leaflet braces 18, 20 can be used as an annuloplasty device. Alternatively, the physician can then deploy a transcatheter heart valve via valve delivery catheter 28 as shown in FIG. 5E. As above for other implementations, the transcatheter heart valve 38 can be mounted on a stent 32. It can be self-expandable, mechanically-expandable or expanded by balloon 30. FIG. 5F shows the heart after completion of the procedure using fastener hoop 268.

Figure 6B:
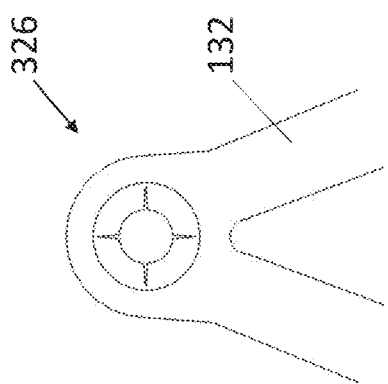
FIG. 6B is an enlarged top view of the boxed area of FIG. 6A showing the detail of a fastener on the fastener stent.

In another implementation, such as the one seen in FIGS. 6A-6C, fasteners 326 can be mounted directly onto a fastening stent 132. FIGS. 6A and 6B illustrate one implementation of the fastener stent 326. When deployed, the fasteners 326 are positioned on the atrial edge of the stent 132. The fasteners 326 and stent 132 can be one piece, or they can be separate pieces joined after forming. The fastening stent 132 can be made of a shape memory material. For example, the shape memory material can be Nitinol. In this implementation, the leaflet braces 18, 20 are not directly connected to one another, but instead are attached to the fastening stent 132 supporting the heart valve 38 as seen in FIG. 6C.

Figure 6D:
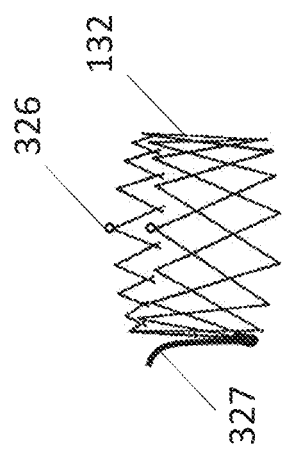
FIG. 6D is a perspective view of the fastener stent of FIG. 6A.
Figure 6E:
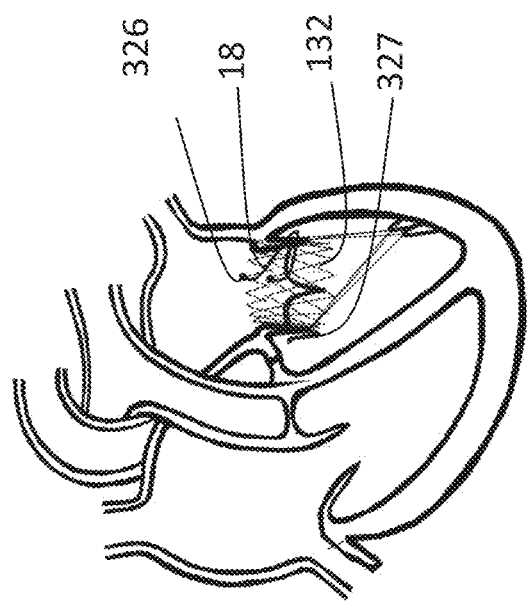
FIG. 6E is a cross-sectional schematic of a heart with the leaflet brace, the fastener stent and an anchor.

For this implementation, securement of just one leaflet can be sufficient. FIG. 6D shows fasteners 326 mounted directly onto a fastening stent 132. This stent also includes an anchor 327. As described in the disclosure of U.S. Pat. No. 8,926,691 (which is hereby incorporated herein by reference), the anchor 327 can be used to capture one of the leaflets of the mitral valve as the stent expands. The leaflet braces disclosed herein can be used to attach the other leaflet. FIG. 6E shows the heart after completion of the procedure using leaflet brace 18, the fastening stent 132, and the anchor 327. The anchor can have a petal-like shape, similar to those shown in the '691 patent used to attach to the anterior leaflet, whereas in this implementation they attach to the posterior leaflet.

Figure 7A:
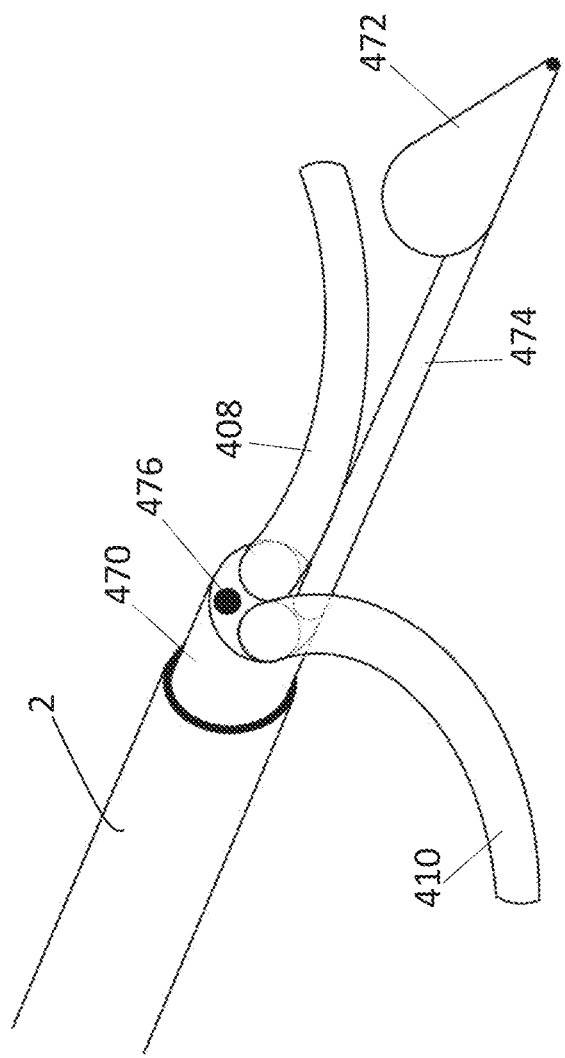
FIG. 7A is a perspective view of a sub-commissural catheter in a transseptal introducer sheath.

As shown in FIGS. 7A-7O, other implementations of the method can use a sub-commissural catheter 470 to assist in steering the guide wires 9, 11, 14, 16 behind their respective leaflets. The sub-commisural catheter 470 as seen in FIG. 7A includes four lumens. The first and second lumens house first and second commissural extensions 408 and 410. A third lumen houses a valve guide wire 474 terminating in a nose cone 472. A fourth lumen houses an internal deflection wire, the anchor point 476 of which can be seen at the distal face of the sub-commissural catheter 470. Pulling on the proximal end of the internal deflection wire causes the sub-commissural catheter to bend.

Figure 7B:
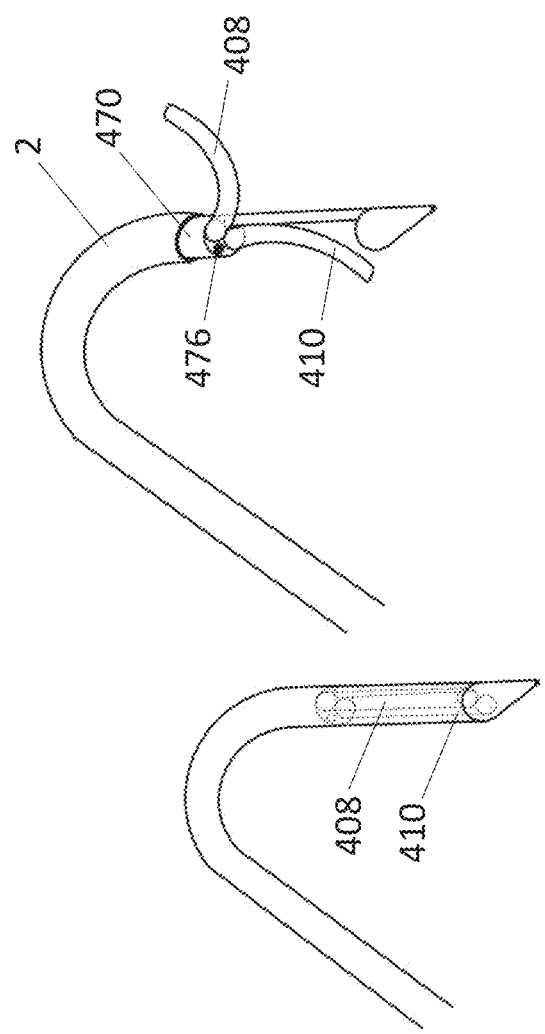
FIG. 7B shows perspective views of the sub-commissural catheter of FIG. 7A with sub-commissural extensions in both retracted and deployed states.

FIG. 7B depicts the system in a bent state. The bending allows it to curve in the left atrium and enter the left ventricle. The physician pulls back on the transseptal introducer sheath 2 to release the commissural extensions 408, 410. The extensions extend in opposite directions, such that an end of each can be positioned beneath the two mitral valve commissures.

Figure 7C:
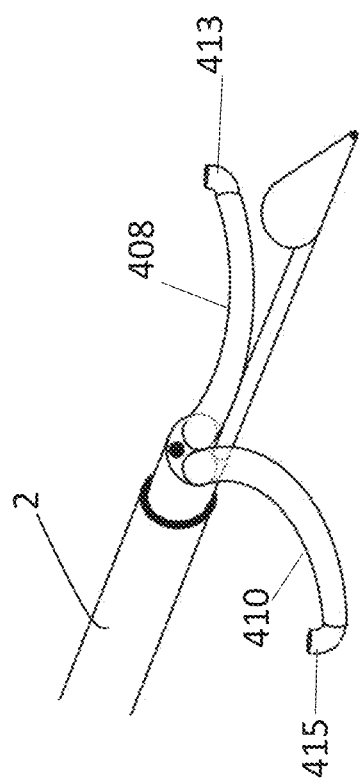
FIG. 7C is a perspective view of the sub-commissural catheter of FIG. 7B with right angle guide catheters deployed.
Figure 7D:
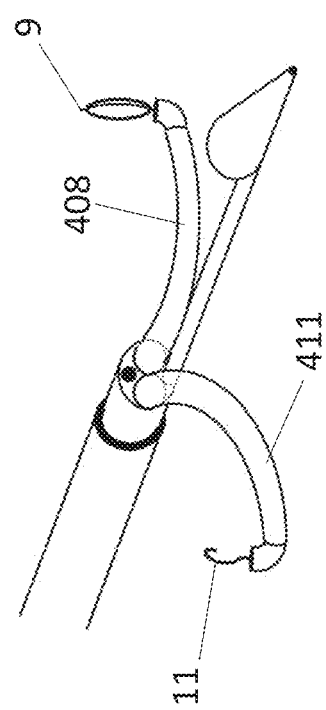
FIG. 7D is a perspective view of the sub-commissural catheter of FIG. 7C with ringed and snare guide wires deployed.

The extensions 408, 410 can house right angle guide catheters 413, 415, as shown in FIG. 7C. The physician can rotate the guide catheters to face either the anterior or posterior leaflets 6, 7. The physician can then deploy ringed guide wires 9, 14 and corresponding snare wires 11, 16 through the right angle guide catheters as shown in FIG. 7D.

Figure 7E:
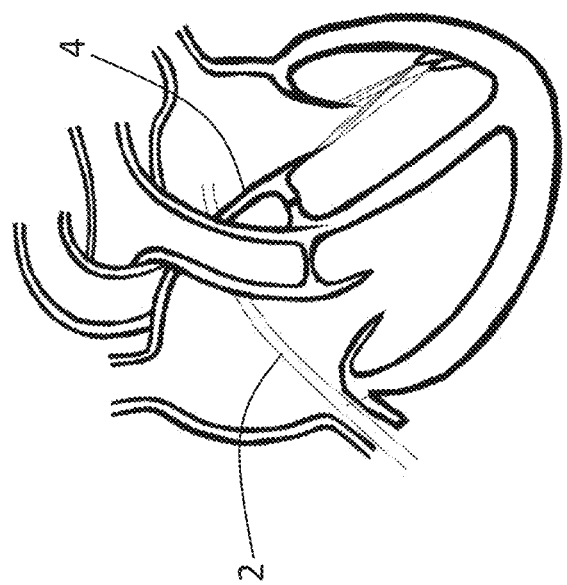
FIG. 7E is a cross-sectional schematic of a heart undergoing a minimally invasive mitral valve procedure after introduction of the transseptal introducer sheath of FIG. 7A-7D.
Figure 7F:
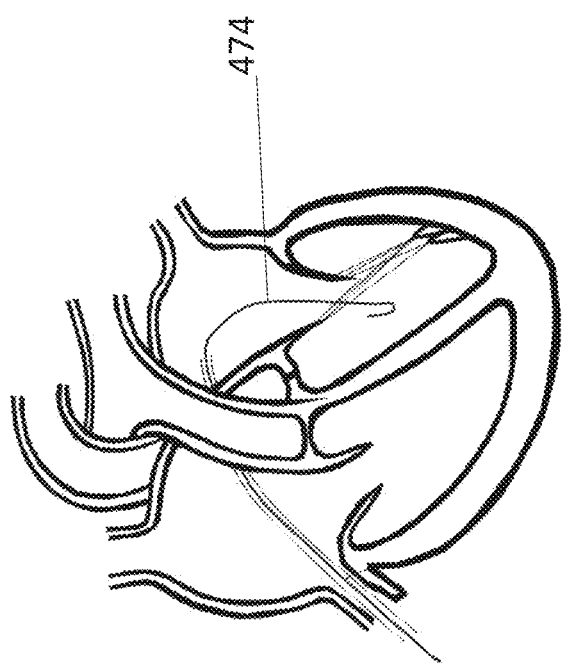
FIG. 7F is a cross-sectional schematic of the heart of FIG. 7E after introduction of a valve guide wire.
Figure 7G:
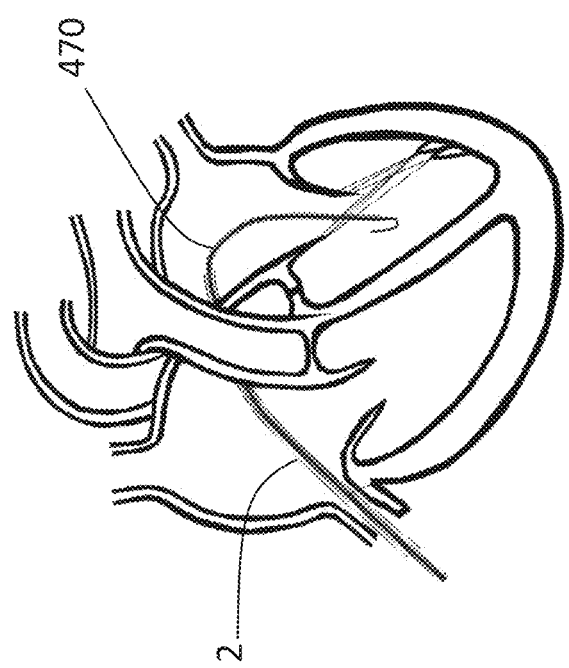
FIG. 7G is a cross-sectional schematic of the heart of FIG. 7F after introduction of a sub-commissural catheter over the valve guide wire.
Figure 7H:
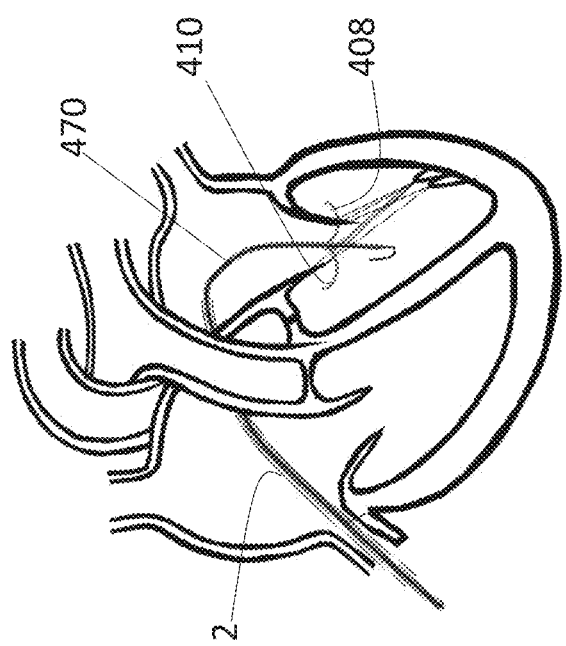
FIG. 7H is a cross-sectional schematic of the heart of FIG. 7G with the commissural extensions deployed from the sub-commissural catheter.
Figure 7I:
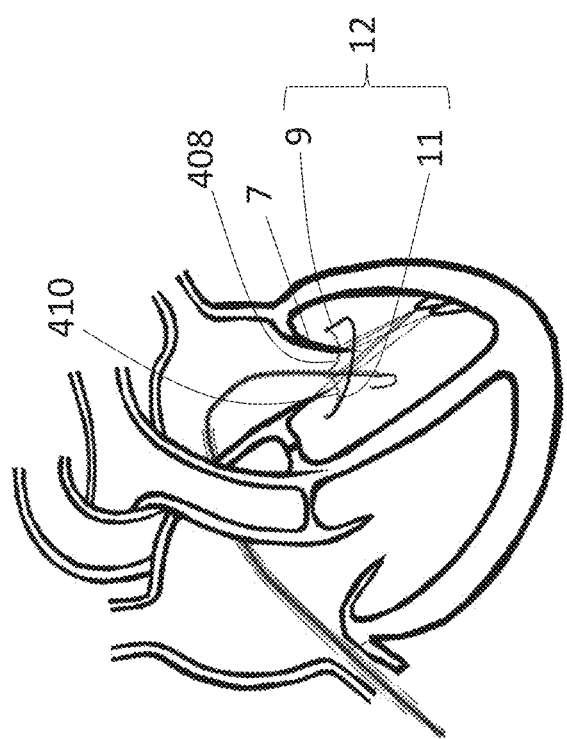
FIG. 7I is a cross-sectional schematic of the heart of FIG. 7H after formation of a guide wire loop around the posterior leaflet.

FIGS. 7E-7O depict a procedure using the sub-commissural catheter 470. The physician first punctures the interatrial septum 4 using the transseptal introducer sheath 2 such that the distal end of the introducer sheath is within the left atrium, as shown in FIG. 7E. The physician then advances a valve delivery guidewire 474 through the introducer sheath, through the mitral valve, and into the left ventricle, as seen in FIG. 7F. The sub-commissural catheter 470 advances over the guide wire 474 to a point below the valve, as seen in FIG. 7G. The physician then pulls back on the transseptal introducer sheath 2 to deploy the commissural extensions 408, 410 as seen in FIG. 7H. The catheter 470 is twisted to position one extension end beneath each of the commissures of the mitral valve. The physician can position a guide wire in the coronary sinus to assist in the orientation of the commissural extensions.

Figure 7J:
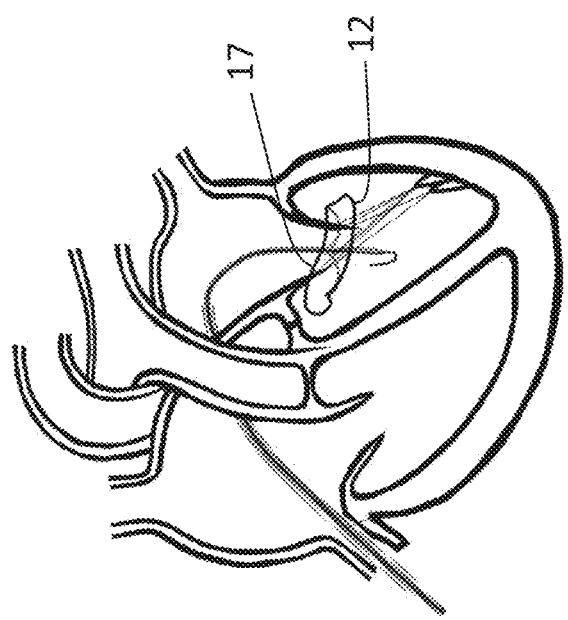
FIG. 7J is a cross-sectional schematic of the heart of FIG. 7I after formation of a guide wire loop around the anterior leaflet.
Figure 7K:
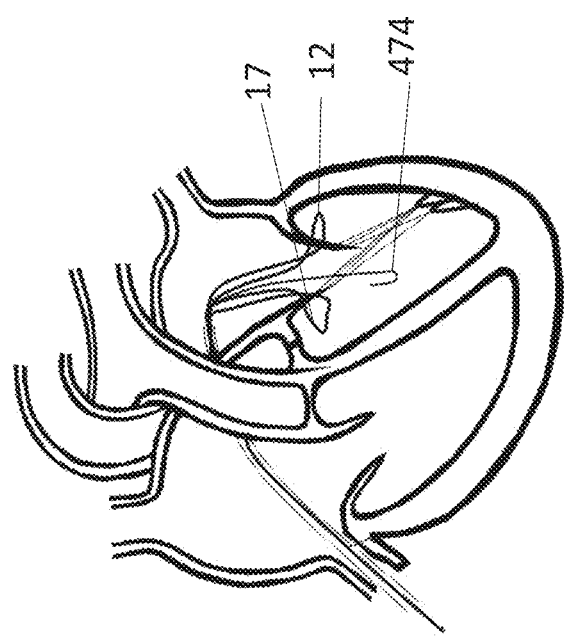
FIG. 7K is a cross-sectional schematic of the heart of FIG. 7J after retraction of the sub-commissural catheter.

The physician then deploys the first ringed guide wire 9 and first snare wire 11 and connects them behind the leaflet. The snared distal end of the ringed guide wire 9 is pulled back into the sub-commissural catheter 470 and all the way out of the proximal end of the catheter 470. This forms the posterior leaflet wire loop 12 shown in FIG. 7I. The physician can then rotate the right angle guide catheters 13, 15 to face the opposite leaflet. The physician can then deploy a second set of ring and snare guide wires to form an anterior leaflet wire loop 17, as seen in FIG. 7J. The sub-commissural catheter 470 and extensions 408, 410 are then removed, leaving behind the wire loops as shown in FIG. 7K.

Figure 7L:
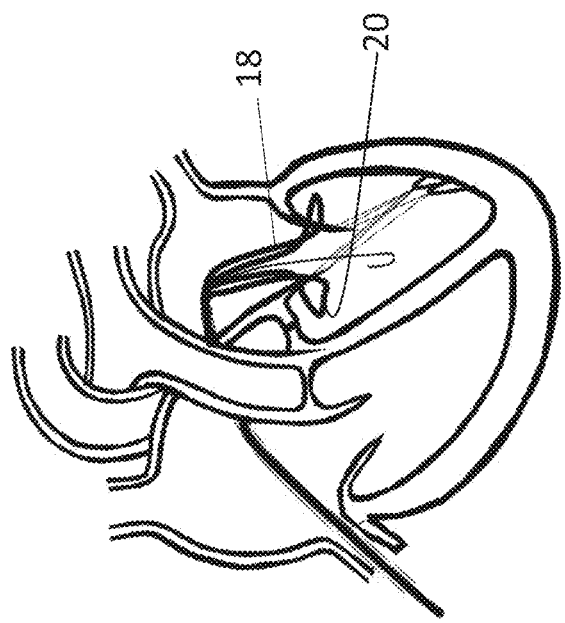
FIG. 7L is a cross-sectional schematic of the heart of FIG. 7K after deployment of the leaflet braces around the guide wire loops.
Figure 7M:
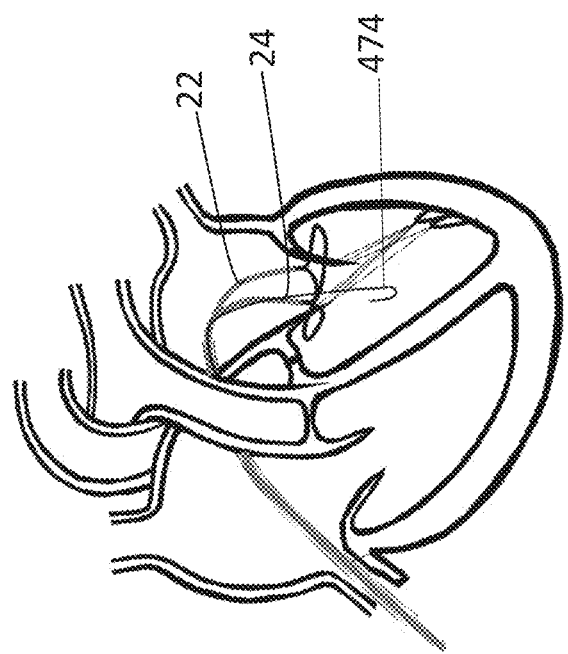
FIG. 7M is a cross-sectional schematic of the heart of FIG. 7L after introduction of fastening catheters over the leaflet braces.

The physician then slides the radiopaque leaflet braces 18, 20 down the guide wires and positions them along posterior and anterior leaflet wire loops 12, 17, as seen in FIG. 7L. He or she then moves the anterolateral and a posteromedial fastening catheters 22, 24 along the guide wires and positions them over the leaflet braces 18, 20, as seen in FIG. 7M. Various implementations of fasteners, such as (but not limited to) those described herein, can be used to join the two leaflet braces. For example, fasteners including screws, latches, clips, or knots can be used to secure the leaflet braces 18, 20.

Figure 7N:
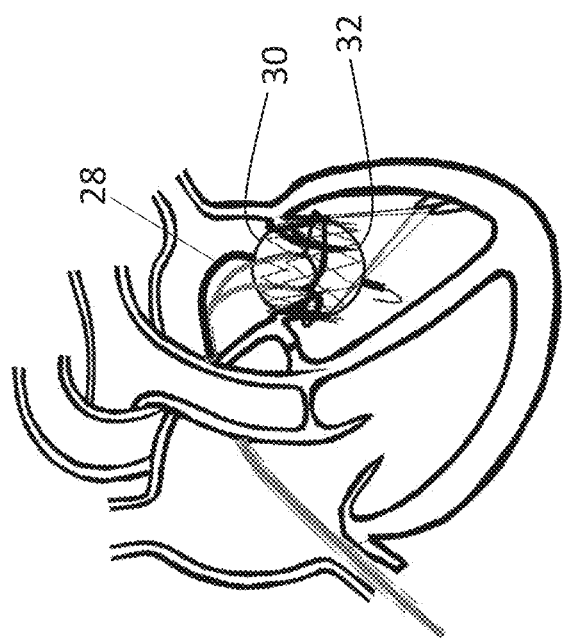
FIG. 7N is a cross-sectional schematic of the heart of FIG. 7M after expansion of a balloon inflatable stented heart valve.
Figure 70:
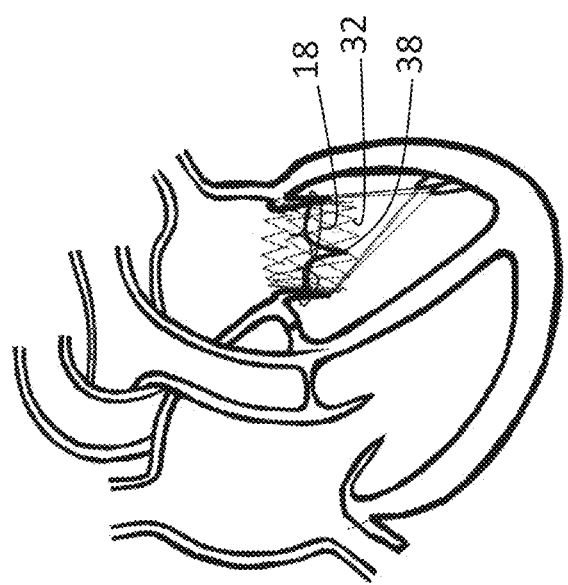

The physician can then tear away the excess tubing from the leaflet braces and retract it back through the transseptal introducer sheath 2. The two braces now form one annular ring circling the valve under the anterior and posterior leaflets 6, 7. The physician can then insert valve delivery catheter 28 and deploy a transcatheter heart valve 38. FIG. 7N depicts an inflated balloon 30 positioned between the mitral valve leaflets to open a transcatheter heart valve 38. Alternatively, or in addition, the valve can be mechanically-expandable or self-expanding. The transcatheter heart valve 38 can be mounted on a stent 32.

After delivering the valve, the physician releases the fasteners 26 from the fastening catheters 22, 24 and retracts the fastening catheters and balloon delivery catheter 28 back up the transseptal introducer sheath 2. The transseptal introducer sheath 2 is then removed from the patient, completing the procedure as shown in FIG. 7O.

In the event that the procedure must be prematurely aborted, the leaflet braces 18, 20 can be retrieved back through the transseptal introducer sheath 2. If the leaflet braces are attached to each other by a metal fastener 26 at only one commissure, the entire system can still be retrieved via the transseptal introducer sheath 2.

Figure 8:
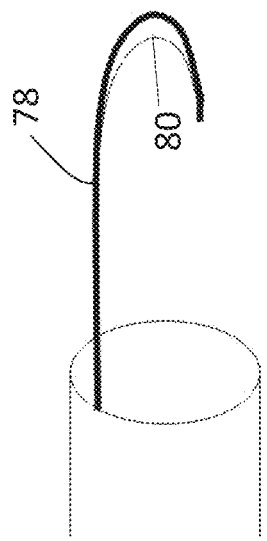
FIG. 8 shows a schematic of a tool for cutting leaflet braces.

If the braces are attached to each other at both commissures and/or secured to the myocardium with barb, they can be cut to be retrieved. FIG. 8 depicts a tool for cutting the leaflet braces 18, 20. The tool includes a J-curved steel hook 78 with a curved blade 80. Using a tube cutting catheter and fluoroscopic imaging techniques, the physician can advance the hook 78 and position the curved blade 80 over the leaflet brace 18, 20. The physician then pulls the hook 78 back into the catheter with force to sever the brace and abort the procedure.

Although the disclosure has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments. In addition, while a particular feature of the disclosure may have been described above with respect to only one or more of several illustrated embodiments, such feature may be combined with one or more other features of the other embodiments, as may be desired and advantageous for any given or particular application.

What is claimed is:

1. A system for repairing a heart valve having at least first and second native leaflets, the system comprising:
   at least one fastening catheter having a distal end;
   at least one fastener comprising first and second openings, wherein the at least one fastener comprises a plurality of locking tabs disposed in the first and second openings; and
   at least one leaflet brace configured to extend at least partially around the first native leaflet;
   wherein the at least one fastening catheter is configured to advance the at least one fastener over the at least one leaflet brace with the at least one leaflet brace extending through one of the openings in the fastener.

2. The system of claim 1, wherein the at least one leaflet brace comprises a first leaflet brace and a second leaflet brace, and wherein the first and second leaflet braces are configured to extend through the first and second openings of the at least one fastener, respectively.

3. The system of claim 2, wherein the at least one fastener comprises a first fastener and a second fastener, and wherein respective first end portions of the first leaflet brace and the second leaflet brace are configured to extend through first and second openings of the first fastener, respectively, and respective second end portions of the first leaflet brace and the second leaflet brace are configured to extend through first and second openings of the second fastener, respectively.

4. The system of claim 3, wherein the at least one fastening catheter comprises a first fastening catheter and a second fastening catheter, wherein the first fastening catheter is configured to advance the first fastener over the first end portions of the first leaflet brace and the second leaflet brace and the second fastening catheter is configured to advance the second fastener over the second end portions of the first leaflet brace and the second leaflet brace.

5. The system of claim 1, wherein the at least one leaflet brace comprises an abutment surface configured to stop advancement of the at least one fastener over the at least one leaflet brace.

6. A system for repairing a heart valve having at least first and second native leaflets, the system comprising:
   at least one fastening catheter having a distal end;
   at least one fastener comprising first and second openings; and
   at least one leaflet brace configured to extend at least partially around the first native leaflet;
   wherein the at least one fastening catheter is configured to advance the at least one fastener over the at least one leaflet brace with the at least one leaflet brace extending through one of the openings in the fastener;
   wherein the at least one leaflet brace comprises a shortening mechanism.

7. The system of claim 6, wherein the shortening mechanism comprises at least one tear notch.

8. A system for repairing a heart valve having at least first and second native leaflets, the system comprising:
   at least one fastening catheter having a distal end;
   at least one fastener comprising first and second openings; and
   at least one leaflet brace configured to extend at least partially around the first native leaflet;
   wherein the at least one fastening catheter is configured to advance the at least one fastener over the at least one leaflet brace with the at least one leaflet brace extending through one of the openings in the fastener;
   wherein the at least one leaflet brace comprises a first leaflet brace and a second leaflet brace;
   wherein the at least one fastener comprises a first fastener and a second fastener, and wherein respective first end portions of the first leaflet brace and the second leaflet brace are configured to extend through first and second openings of the first fastener, respectively, and respective second end portions of the first leaflet brace and the second leaflet brace are configured to extend through first and second openings of the second fastener, respectively;
   a fastener hoop connected to the first fastener and the second fastener.

9. A system for repairing a heart valve having at least first and second native leaflets, the system comprising:
   a first fastener;
   a second faster;
   a first leaflet brace having a first end portion and a second end portion, wherein the first leaflet brace is configured to extend partially around the first native leaflet; and
   a second leaflet brace having a first end portion and a second end portion, wherein the second leaflet brace is configured to extend partially around the second native leaflet;
   wherein the first fastener is configured to be deployed on the first end portion of the first leaflet brace and the first end portion of the second leaflet brace so as to connect the first end portions to each other;
   wherein the second fastener is configured to be deployed on the second end portion of the first leaflet brace and the second end portion of the second leaflet brace so as to connect the second end portions to each other;
   wherein, when the first end portions are connected to each other and the second end portions are connected to each other, the first and second leaflet braces form a closed annular ring that completely encircles the first and second native leaflets.

10. The system of claim 9, further comprising a first fastening catheter and a second fastening catheter, wherein the first fastening catheter is configured to position the first fastener over the first end portion of the first leaflet brace and the first end portion of the second leaflet brace, and the second fastening catheter is configured to position the second fastener over the second end portion of the first leaflet brace and the second end portion of the second leaflet brace.

11. The system of claim 10, wherein the first fastener is releasably coupled to a distal end of the first fastening catheter and the second fastener is releasably coupled to a distal end of the second fastening catheter.

12. The system of claim 9, wherein the first fastener comprises first and second openings sized to receive the first end portion of the first leaflet brace and the first end portion of the second leaflet brace, respectively.

13. The system of claim 12, wherein the second fastener comprises first and second openings sized to receive the second end portion of the first leaflet brace and the second end portion of the second leaflet brace, respectively.

14. The system of claim 12, wherein the first fastener comprises a plurality of locking tabs arranged within the first and second openings and configured to engage outer surfaces of the first and second leaflet braces.

15. The system of claim 13, wherein the second fastener comprises a plurality of locking tabs arranged within the first and second openings and configured to engage outer surfaces of the first and second leaflet braces.

16. The system of claim 9, wherein the first fastener comprises one or more fastener barbs configured to be pushed into adjacent tissue in the heart.

17. A system for repairing a heart valve having at least first and second native leaflets, the system comprising:
   a first fastener;
   a second faster;
   a first leaflet brace having a first end portion and a second end portion, wherein the first leaflet brace is configured to extend partially around the first native leaflet; and
   a second leaflet brace having a first end portion and a second end portion, wherein the second leaflet brace is configured to extend partially around the second native leaflet;
   wherein the first fastener is configured to be deployed on the first end portion of the first leaflet brace and the first end portion of the second leaflet brace so as to connect the first end portions to each other;
   wherein the second fastener is configured to be deployed on the second end portion of the first leaflet brace and the second end portion of the second leaflet brace so as to connect the second end portions to each other;
   wherein, when the first end portions are connected to each other and the second end portions are connected to each other, the first and second leaflet braces encircle the first and second native leaflets;
   wherein the first end portions and second end portions of the first leaflet brace and the second leaflet brace comprise tear notches for removing excess portions of the leaflet braces.

18. A system for repairing a heart valve having at least first and second native leaflets, the system comprising:
   a first fastener;
   a second faster;

a first leaflet brace having a first end portion and a second end portion, wherein the first leaflet brace is configured to extend partially around the first native leaflet; and a second leaflet brace having a first end portion and a second end portion, wherein the second leaflet brace is configured to extend partially around the second native leaflet;

wherein the first fastener is configured to be deployed on the first end portion of the first leaflet brace and the first end portion of the second leaflet brace so as to connect the first end portions to each other;

wherein the second fastener is configured to be deployed on the second end portion of the first leaflet brace and the second end portion of the second leaflet brace so as to connect the second end portions to each other;

wherein, when the first end portions are connected to each other and the second end portions are connected to each other, the first and second leaflet braces encircle the first and second native leaflets;

wherein the first end portions of the first and second leaflet braces each comprises a first section having a first diameter and a second section having a second diameter, greater than the first diameter, wherein the first fastener can be deployed on the first sections of the first and second leaflet braces and the second sections of the first and second leaflet braces limit movement of the first fastener along the first and second leaflet braces in one direction.

19. A system for repairing a heart valve having at least first and second native leaflets, the system comprising:

a first leaflet brace having a first end portion and a second end portion, wherein the first leaflet brace is configured to extend partially around the first native leaflet; and a second leaflet brace having a first end portion and a second end portion, wherein the second leaflet brace is configured to extend partially around the second native leaflet;

a first fastener comprising first and second openings sized to receive the first end portion of the first leaflet brace and the first end portion of the second leaflet brace, respectively;

a second faster comprises first and second openings sized to receive the second end portion of the first leaflet brace and the second end portion of the second leaflet brace, respectively;

a first fastening catheter is configured to advance the first fastener over the first end portion of the first leaflet brace and the first end portion of the second leaflet brace; and a second fastening catheter is configured to advance the second fastener over the second end portion of the first leaflet brace and the second end portion of the second leaflet brace.

20. The system of claim 9, further comprising a valve delivery catheter and a transcatheter heart valve, wherein the valve delivery catheter is configured to implant the transcatheter heart valve between the first and second native leaflets, wherein the transcatheter heart valve is radially expandable to an expanded state in which the first and second native leaflets are trapped between the transcatheter heart valve and the leaflet braces.

* * * * *